United States Patent
Jones

(10) Patent No.: US 11,737,906 B2
(45) Date of Patent: Aug. 29, 2023

(54) ADJUSTABLE CONVEX OSTOMY DEVICE

(71) Applicant: CONVATEC TECHNOLOGIES INC., Las Vegas, NV (US)

(72) Inventor: James D. Jones, Bridgewater, NJ (US)

(73) Assignee: ConvaTec Technologies, Inc., Las Vegas, NV (US)

( * ) Notice: Subject to any disclaimer, the term of this patent is extended or adjusted under 35 U.S.C. 154(b) by 378 days.

(21) Appl. No.: 16/784,528

(22) Filed: Feb. 7, 2020

(65) Prior Publication Data

US 2020/0253777 A1 Aug. 13, 2020

Related U.S. Application Data

(60) Provisional application No. 62/802,631, filed on Feb. 7, 2019.

(51) Int. Cl.
*A61F 5/448* (2006.01)
*A61F 5/44* (2006.01)
*A61F 5/443* (2006.01)

(52) U.S. Cl.
CPC .............. *A61F 5/443* (2013.01); *A61F 5/448* (2013.01); *A61F 2005/4483* (2013.01)

(58) Field of Classification Search
CPC ... A61F 5/443; A61F 5/448; A61F 2005/4483
See application file for complete search history.

(56) References Cited

U.S. PATENT DOCUMENTS

| | | | | |
|---|---|---|---|---|
| 3,970,085 A | * | 7/1976 | Mersan | A61F 5/445 604/339 |
| 4,419,100 A | * | 12/1983 | Alexander | A61F 5/448 604/339 |
| 4,592,750 A | * | 6/1986 | Kay | A61F 5/4407 604/277 |
| 4,596,566 A | * | 6/1986 | Kay | A61F 5/4404 604/176 |
| 4,610,676 A | * | 9/1986 | Schneider | A61F 5/448 604/339 |
| 4,834,731 A | * | 5/1989 | Nowak | A61F 5/448 604/339 |
| 4,950,223 A | * | 8/1990 | Silvanov | A61F 5/441 600/32 |
| 4,973,323 A | * | 11/1990 | Kaczmarek | A61F 5/448 604/277 |

(Continued)

FOREIGN PATENT DOCUMENTS

| | | |
|---|---|---|
| DE | 20012498 U1 | 11/2001 |
| EP | 3541331 | 8/2021 |

(Continued)

OTHER PUBLICATIONS

US 10,806,622 B2, 10/2020, Hansen et al. (withdrawn)
Search Opinion for European Patent Application No. 20275026.1; dated May 27, 2020; 2 pages.

*Primary Examiner* — Guy K Townsend
(74) *Attorney, Agent, or Firm* — Taft Stettinius & Hollister LLP; Ryan O. White; Derek B. Lavender

(57) ABSTRACT

Certain embodiments of the present application relate to an adjustable ostomy wafer system including an ostomy wafer and an insert ring 100. The ostomy wafer includes an adjustable layer with an effluent opening through which effluent flows, and the adjustable layer has a body-facing side and a non-body-facing side. The insert ring 100 is capable of providing or increasing convexity of the adjustable layer when the insert ring 100 is pressed against the non-body-facing side of the adjustable layer.

25 Claims, 5 Drawing Sheets

(56) References Cited

U.S. PATENT DOCUMENTS

| | | | |
|---|---|---|---|
| 5,004,464 A * | 4/1991 | Leise, Jr. | A61F 5/448 604/338 |
| 5,163,930 A * | 11/1992 | Blum | A61F 5/448 604/338 |
| 5,195,996 A * | 3/1993 | Edwards | A61F 5/448 604/338 |
| 5,257,981 A * | 11/1993 | Takahashi | A61F 5/448 604/338 |
| 5,429,625 A * | 7/1995 | Holmberg | A61F 5/448 604/338 |
| 5,607,413 A * | 3/1997 | Holmberg | A61F 5/448 604/338 |
| 6,071,268 A * | 6/2000 | Wagner | A61F 5/445 604/338 |
| 6,210,384 B1 * | 4/2001 | Cline | A61F 5/448 604/338 |
| 6,689,111 B2 * | 2/2004 | Mulhauser | A61F 5/445 604/332 |
| 6,740,067 B2 * | 5/2004 | Leise, Jr. | A61F 5/448 604/336 |
| 6,840,924 B2 * | 1/2005 | Buglino | A61F 5/448 604/344 |
| 7,347,844 B2 * | 3/2008 | Cline | A61F 5/448 604/338 |
| 7,857,796 B2 * | 12/2010 | Cline | A61F 5/448 604/277 |
| 8,449,513 B2 | 5/2013 | Abrams | |
| 8,845,606 B2 * | 9/2014 | Nguyen-Demary | A61F 5/445 604/338 |
| 8,979,811 B2 | 3/2015 | Keleny et al. | |
| 8,998,862 B2 * | 4/2015 | Hanuka | A61F 5/4405 604/318 |
| 8,998,867 B2 * | 4/2015 | Sabeti | A61F 5/4405 604/335 |
| 9,345,612 B2 * | 5/2016 | Hanuka | A61F 5/448 |
| 9,943,436 B2 * | 4/2018 | Nguyen-Demary | A61F 5/445 |
| 9,968,480 B2 | 5/2018 | Nyberg | |
| 10,278,857 B2 | 5/2019 | Hansen et al. | |
| 10,335,509 B2 * | 7/2019 | Kutsukake | A61L 15/44 |
| D862,691 S | 10/2019 | Fenton | |
| 10,434,015 B2 | 10/2019 | Taylor et al. | |
| 10,434,309 B2 | 10/2019 | Forsell | |
| 10,449,081 B2 | 10/2019 | Lee | |
| 10,449,082 B2 | 10/2019 | Johnsen | |
| 10,463,527 B2 | 11/2019 | Gallant et al. | |
| 10,470,917 B2 | 11/2019 | Chang | |
| 10,470,918 B2 | 11/2019 | Bendix | |
| 10,471,173 B2 | 11/2019 | Misawa | |
| 10,478,328 B2 | 11/2019 | Guidry et al. | |
| 10,478,329 B2 | 11/2019 | Oberholtzer et al. | |
| 10,478,330 B2 | 11/2019 | Wiltshire et al. | |
| 10,500,084 B2 | 12/2019 | Hansen et al. | |
| 10,500,315 B2 | 12/2019 | Chang et al. | |
| 10,507,318 B2 | 12/2019 | Jin et al. | |
| 10,512,562 B2 | 12/2019 | Kavanagh et al. | |
| 10,524,953 B2 * | 1/2020 | Hanuka | A61F 5/4404 |
| 10,531,978 B2 | 1/2020 | Haas et al. | |
| 10,537,461 B2 * | 1/2020 | Hanuka | A61F 5/441 |
| 10,537,462 B1 | 1/2020 | Hatchett et al. | |
| 10,583,029 B2 | 3/2020 | Chang | |
| 10,588,773 B2 | 3/2020 | Tsai et al. | |
| 10,610,402 B1 | 4/2020 | Idowu et al. | |
| 10,617,554 B2 | 4/2020 | Luce | |
| 10,617,555 B2 | 4/2020 | James et al. | |
| 10,646,370 B2 | 5/2020 | Keleny et al. | |
| 10,653,551 B2 * | 5/2020 | Apolinario | A61F 5/441 |
| 10,660,784 B2 | 5/2020 | Nishtala et al. | |
| 10,660,785 B2 | 5/2020 | Kaufman et al. | |
| 10,660,786 B2 | 5/2020 | Obst et al. | |
| 10,729,806 B2 | 8/2020 | Bingol et al. | |
| 10,736,769 B2 | 8/2020 | Grove Sund et al. | |
| 10,744,224 B2 | 8/2020 | Israelson et al. | |
| 10,758,398 B2 | 9/2020 | Murthy Aravalli et al. | |
| 10,779,986 B2 | 9/2020 | Cox | |
| 10,799,385 B2 | 10/2020 | Hansen et al. | |
| 10,813,786 B2 | 10/2020 | Lysgaard | |
| 10,813,787 B2 | 10/2020 | Dinakara et al. | |
| 2003/0088219 A1 * | 5/2003 | Metz | A61F 5/448 604/339 |
| 2004/0006320 A1 * | 1/2004 | Buglino | A61F 5/448 604/344 |
| 2004/0193122 A1 * | 9/2004 | Cline | A61F 5/448 604/332 |
| 2004/0267216 A1 | 12/2004 | Udayakumar et al. | |
| 2005/0054997 A1 * | 3/2005 | Buglino | A61F 5/448 604/332 |
| 2006/0058576 A1 | 3/2006 | Davies et al. | |
| 2006/0206069 A1 * | 9/2006 | Cline | A61F 5/445 604/332 |
| 2008/0119804 A1 * | 5/2008 | Cline | A61F 5/445 604/338 |
| 2010/0174253 A1 | 7/2010 | Cline et al. | |
| 2011/0218507 A1 | 9/2011 | Andersen et al. | |
| 2012/0041400 A1 | 2/2012 | Christensen | |
| 2012/0059341 A1 * | 3/2012 | Masters | A61F 5/448 604/339 |
| 2012/0109086 A1 | 5/2012 | Tsai | |
| 2012/0136324 A1 * | 5/2012 | Hanuka | A61F 5/441 604/318 |
| 2012/0179124 A1 | 7/2012 | Nguyen-Demary et al. | |
| 2013/0030397 A1 * | 1/2013 | Sabeti | A61F 5/4405 604/338 |
| 2013/0072886 A1 | 3/2013 | Schertiger et al. | |
| 2013/0226063 A1 | 8/2013 | Taylor et al. | |
| 2014/0207094 A1 | 7/2014 | Chang | |
| 2014/0221950 A1 | 8/2014 | Chang et al. | |
| 2014/0288517 A1 | 9/2014 | Tsai et al. | |
| 2014/0316360 A1 | 10/2014 | Ekfeldt et al. | |
| 2014/0324002 A1 * | 10/2014 | Luce | A61F 5/441 604/338 |
| 2015/0133881 A1 | 5/2015 | Freiding | |
| 2015/0209172 A1 | 7/2015 | Richmann et al. | |
| 2016/0074206 A1 * | 3/2016 | Nassopoulos | A61F 5/445 604/338 |
| 2016/0151198 A1 | 6/2016 | Frampton et al. | |
| 2016/0193003 A1 | 7/2016 | Todd et al. | |
| 2016/0206469 A1 | 7/2016 | Prezelin | |
| 2016/0302959 A1 * | 10/2016 | Kavanagh | A61F 5/449 |
| 2017/0007440 A1 | 1/2017 | Moavenian | |
| 2017/0065451 A1 | 3/2017 | Brandt et al. | |
| 2017/0209295 A1 | 7/2017 | Smith et al. | |
| 2017/0209296 A1 | 7/2017 | Cailleteau | |
| 2018/0064572 A1 | 3/2018 | Wiltshire | |
| 2018/0235801 A1 | 8/2018 | Oellgaard et al. | |
| 2018/0236207 A1 | 8/2018 | Shankarsetty | |
| 2018/0303655 A1 | 10/2018 | Glithero et al. | |
| 2018/0311066 A1 | 11/2018 | Hansen et al. | |
| 2018/0333290 A1 * | 11/2018 | Jones | A61F 5/441 |
| 2018/0344506 A1 | 12/2018 | Larsen | |
| 2018/0360644 A1 | 12/2018 | Alvarez Ponce | |
| 2018/0369474 A1 | 12/2018 | Falleboe et al. | |
| 2019/0015241 A1 | 1/2019 | Lin et al. | |
| 2019/0029868 A1 | 1/2019 | Grum-Schwensen et al. | |
| 2019/0110919 A1 | 4/2019 | Beckers et al. | |
| 2019/0117824 A1 | 4/2019 | Hansen et al. | |
| 2019/0231580 A1 * | 8/2019 | Czaplewski | A61F 5/445 |
| 2019/0247549 A1 | 8/2019 | Nielsen | |
| 2019/0254864 A1 * | 8/2019 | Czaplewski | A61F 5/451 |
| 2019/0321213 A1 | 10/2019 | Morrison, Sr. | |
| 2019/0328571 A1 | 10/2019 | Adachi | |
| 2019/0328572 A1 | 10/2019 | Weinberg et al. | |
| 2019/0358076 A1 | 11/2019 | Blatt | |
| 2019/0365560 A1 | 12/2019 | Timms et al. | |
| 2019/0374372 A1 | 12/2019 | Seres et al. | |
| 2019/0380860 A1 * | 12/2019 | Eggert | A61F 5/4405 |
| 2019/0380861 A1 | 12/2019 | Nordquist et al. | |
| 2019/0380882 A1 | 12/2019 | Taylor et al. | |
| 2020/0000624 A1 | 1/2020 | Gibbons et al. | |
| 2020/0015996 A1 | 1/2020 | Schertiger | |
| 2020/0030134 A1 | 1/2020 | Hopper | |
| 2020/0038226 A1 | 2/2020 | Botten et al. | |

(56) References Cited

U.S. PATENT DOCUMENTS

| | | |
|---|---|---|
| 2020/0038227 A1 | 2/2020 | Makar, Jr. |
| 2020/0038228 A1 | 2/2020 | Aravalli et al. |
| 2020/0038229 A1 | 2/2020 | Aravalli |
| 2020/0046541 A1 | 2/2020 | Sund et al. |
| 2020/0046542 A1 | 2/2020 | Guidry et al. |
| 2020/0046543 A1 | 2/2020 | Scalise et al. |
| 2020/0054476 A1 | 2/2020 | Miller |
| 2020/0054478 A1 | 2/2020 | Forsell |
| 2020/0060863 A1 | 2/2020 | Sund et al. |
| 2020/0061282 A1 | 2/2020 | Hvid et al. |
| 2020/0069455 A1 | 3/2020 | Oberholtzer et al. |
| 2020/0069529 A1 | 3/2020 | Starnes et al. |
| 2020/0078206 A1 | 3/2020 | Chiladakis |
| 2020/0085608 A1 | 3/2020 | Hrushka et al. |
| 2020/0093633 A1 | 3/2020 | Blumrosen et al. |
| 2020/0100931 A1* | 4/2020 | Schoess ............... A61F 5/443 |
| 2020/0100946 A1 | 4/2020 | Wohlgemuth et al. |
| 2020/0121490 A1 | 4/2020 | Woodward et al. |
| 2020/0138618 A1 | 5/2020 | Roszkowiak et al. |
| 2020/0138619 A1 | 5/2020 | Cisko, Jr. et al. |
| 2020/0146944 A1 | 5/2020 | Moulton et al. |
| 2020/0155338 A1 | 5/2020 | Meteer |
| 2020/0163792 A1 | 5/2020 | Schertiger |
| 2020/0164196 A1 | 5/2020 | Jin et al. |
| 2020/0188160 A1 | 6/2020 | Udayakumar |
| 2020/0188161 A1 | 6/2020 | Seres et al. |
| 2020/0188162 A1 | 6/2020 | Menifee |
| 2020/0197213 A1 | 6/2020 | Frampton-Vallance et al. |
| 2020/0214371 A1 | 7/2020 | Apelt |
| 2020/0214872 A1 | 7/2020 | Tretheway et al. |
| 2020/0214873 A1 | 7/2020 | Tretheway et al. |
| 2020/0214875 A1 | 7/2020 | Tretheway et al. |
| 2020/0229962 A1 | 7/2020 | Torstensen et al. |
| 2020/0237550 A1 | 7/2020 | Hussey et al. |
| 2020/0246173 A1 | 8/2020 | Schertiger et al. |
| 2020/0246174 A1 | 8/2020 | Hansen et al. |
| 2020/0246175 A1 | 8/2020 | Hansen et al. |
| 2020/0246176 A1 | 8/2020 | Hansen et al. |
| 2020/0246177 A1 | 8/2020 | Hansen et al. |
| 2020/0246178 A1 | 8/2020 | O'Hamill et al. |
| 2020/0253633 A1 | 8/2020 | Obst et al. |
| 2020/0253777 A1* | 8/2020 | Jones ................. A61F 5/443 |
| 2020/0261254 A1 | 8/2020 | Williams et al. |
| 2020/0276044 A1 | 9/2020 | Tretheway et al. |
| 2020/0276045 A1 | 9/2020 | Bendavit |
| 2020/0281758 A1 | 9/2020 | Tan |
| 2020/0281759 A1 | 9/2020 | Lu |
| 2020/0281761 A1 | 9/2020 | Tretheway et al. |
| 2020/0289307 A1 | 9/2020 | Tretheway et al. |
| 2020/0289308 A1 | 9/2020 | Tretheway et al. |
| 2020/0297524 A1 | 9/2020 | Hunt et al. |
| 2020/0306073 A1 | 10/2020 | Olsen et al. |
| 2020/0306074 A1 | 10/2020 | Speiermann et al. |
| 2020/0330258 A1 | 10/2020 | Hansen et al. |
| 2020/0330259 A1 | 10/2020 | Sund et al. |
| 2020/0330260 A1 | 10/2020 | Hansen et al. |
| 2020/0337879 A1 | 10/2020 | Donovan et al. |
| 2020/0337880 A1 | 10/2020 | Hansen et al. |
| 2020/0337881 A1 | 10/2020 | Hansen et al. |
| 2020/0337882 A1 | 10/2020 | Hansen et al. |
| 2020/0337883 A1 | 10/2020 | Hansen et al. |
| 2020/0337884 A1 | 10/2020 | Donovan et al. |
| 2020/0337885 A1 | 10/2020 | Donovan et al. |
| 2020/0338230 A1 | 10/2020 | Israelson et al. |
| 2021/0307952 A1* | 10/2021 | Nielsen ............... A61F 5/448 |
| 2021/0369492 A1* | 12/2021 | O'Grady ............. A61F 5/445 |

FOREIGN PATENT DOCUMENTS

| | | | |
|---|---|---|---|
| EP | 3912603 A1 | 11/2021 | |
| GB | 2534012 A | 7/2016 | |
| GB | 2544180 A | 5/2017 | |
| GB | 2548673 A | 9/2017 | |
| GB | 2550936 A | 12/2017 | |
| GB | 2570526 A | 7/2019 | |
| GB | 2575687 A | 1/2020 | |
| GB | 2571835 B | 2/2020 | |
| WO | 2015110544 A1 | 7/2015 | |
| WO | 2015138190 A1 | 9/2015 | |
| WO | 2015148035 A1 | 10/2015 | |
| WO | 2018067539 A1 | 4/2018 | |
| WO | WO-2018067539 A1 * | 4/2018 | ............ A61F 5/443 |
| WO | 2018188706 A1 | 10/2018 | |
| WO | 2018188707 A1 | 10/2018 | |
| WO | 2019058126 A1 | 3/2019 | |
| WO | 2019058127 A1 | 3/2019 | |
| WO | 2019091526 A1 | 5/2019 | |
| WO | 2019091527 A1 | 5/2019 | |
| WO | 2019091528 A1 | 5/2019 | |
| WO | 2019091529 A1 | 5/2019 | |
| WO | 2019091532 A1 | 5/2019 | |
| WO | 2019099662 A1 | 5/2019 | |
| WO | 2019120424 A1 | 6/2019 | |
| WO | 2019120429 A1 | 6/2019 | |
| WO | 2019120430 A1 | 6/2019 | |
| WO | 2019120432 A1 | 6/2019 | |
| WO | 2019120433 A1 | 6/2019 | |
| WO | 2019120434 A1 | 6/2019 | |
| WO | 2019120437 A1 | 6/2019 | |
| WO | 2019120438 A1 | 6/2019 | |
| WO | 2019120439 A1 | 6/2019 | |
| WO | 2019120442 A1 | 6/2019 | |
| WO | 2019120443 A1 | 6/2019 | |
| WO | 2019120444 A1 | 6/2019 | |
| WO | 2019120446 A1 | 6/2019 | |
| WO | 2019120448 A1 | 6/2019 | |
| WO | 2019120449 A1 | 6/2019 | |
| WO | 2019120450 A1 | 6/2019 | |
| WO | 2019120451 A1 | 6/2019 | |
| WO | 2019120452 A1 | 6/2019 | |
| WO | 2019120458 A1 | 6/2019 | |
| WO | 2019197291 A1 | 10/2019 | |
| WO | 2019197971 A1 | 10/2019 | |
| WO | 2019198012 A1 | 10/2019 | |
| WO | 2019221830 A1 | 11/2019 | |
| WO | 2019229267 A2 | 12/2019 | |
| WO | 2019229268 A1 | 12/2019 | |
| WO | 2019242828 A1 | 12/2019 | |
| WO | 2020008470 A1 | 1/2020 | |
| WO | 2020010766 A1 | 1/2020 | |
| WO | 2020014305 A1 | 1/2020 | |
| WO | 2020016471 A1 | 1/2020 | |
| WO | 2020035121 A1 | 2/2020 | |
| WO | 2020044081 A1 | 3/2020 | |
| WO | 2020055998 A1 | 3/2020 | |
| WO | 2020076607 A1 | 4/2020 | |
| WO | 2020076609 A1 | 4/2020 | |
| WO | 2020084282 A1 | 4/2020 | |
| WO | 2020125906 A1 | 6/2020 | |
| WO | 2020125907 A1 | 6/2020 | |
| WO | 2020128456 A1 | 6/2020 | |
| WO | 2020128457 A1 | 6/2020 | |
| WO | 2020156624 A1 | 8/2020 | |
| WO | 2020156625 A1 | 8/2020 | |
| WO | 2020156626 A1 | 8/2020 | |
| WO | 2020169162 A1 | 8/2020 | |
| WO | 2020173534 A1 | 9/2020 | |
| WO | 2020174218 A1 | 9/2020 | |
| WO | 2020174219 A1 | 9/2020 | |
| WO | 2020174220 A1 | 9/2020 | |
| WO | 2020174497 A1 | 9/2020 | |
| WO | 2020182923 A1 | 9/2020 | |
| WO | 2020193943 A1 | 10/2020 | |
| WO | 2020200382 A1 | 10/2020 | |
| WO | 2020201718 A1 | 10/2020 | |
| WO | 2020216426 A1 | 10/2020 | |
| WO | 2020216427 A1 | 10/2020 | |
| WO | 2020216429 A1 | 10/2020 | |
| WO | 2020219153 A1 | 10/2020 | |

* cited by examiner

ADJUSTABLE CONVEX OSTOMY DEVICE

CROSS-REFERENCE TO RELATED APPLICATIONS

The present application claims the benefit of U.S. Provisional Patent Application No. 62/802,631, filed 7 Feb. 2019, the contents of which are incorporated by reference in their entirety.

BACKGROUND

There are many forms of ostomy care products which try to provide a secure, comfortable fit for ostomates. There remains a need, however, for ostomy products that fit and seal skin contours, including flush, retracted, prolapsed and irregular shaped stomas. For these instances, there is a need for an ostomy system that is convex in shape to create a good seal at the base of the stoma in order to prevent leakage and protect the skin from stoma output. Current convex stoma systems, however, are complicated and difficult to customize.

SUMMARY

Current convex ostomy wafer products only offer a limited degree of convexity in any given device. In addition, stoma environment and topography may change over time, both suddenly and gradually. Therefore, an ostomate may sometimes require a deep convex wafer, while a shallow convex wafer is preferable at other times. Ideally an ostomate would only have to purchase a single ostomy wafer system that would provide varying levels of convexity depending on their current need. To address this need, ostomy wafers that provide varying levels of convexity are disclosed herein.

In some embodiments, disclosed herein are adjustable ostomy wafer systems, methods and devices. In some instances, the systems, methods and devices comprise an ostomy wafer comprising an adjustable layer, with an effluent opening through which effluent flows; and an insert ring capable of providing or increasing convexity of the adjustable layer when the insert ring is pressed against the non-body-facing side of the adjustable layer.

In some instances, the adjustable ostomy wafer systems comprise an external adhesive layer extending beyond an outer edge of the adjustable layer, wherein the external adhesive layer has an adhesive body-facing side. In other embodiments, the adjustable layer holds the insert ring in place during use to maintain the convexity in the adjustable layer. In yet other instances, the insert ring comprises a groove that engages a portion of the adjustable layer. In some instances, the groove engages an edge of the adjustable layer located proximal to the effluent opening, thereby securing and maintaining a position of the insert ring in the adjustable layer.

In still other instances, the adjustable ostomy wafer systems, devices and methods disclosed herein further comprise a convex insert, wherein a groove of the insert ring of the systems, devices and methods disclosed herein engages the convex insert, thereby securing and maintaining a position of the insert ring in the adjustable layer. In some instances, at least a portion of the convex insert that engages the groove is more rigid than the adjustable layer or a portion thereof. In yet other instances, the adjustable ostomy wafer systems, methods and devices disclosed herein comprise at least one locking tab that engages the groove of the insert ring, maintaining a position of the insert ring in the adjustable layer. In yet other instances, the insert ring comprises a plurality of grooves, wherein each of the grooves corresponds to a different level of convexity of the adjustable layer. In still other instances, the convexity of the adjustable layer is varied between a minimal convexity of about ⅛ inch and a maximal convexity of about 1 inch. In yet other instances, the convexity of the adjustable layer is varied between a minimal convexity of about ½ inch and a maximal convexity of about 1 inch. In some instances, the insert ring is flexible. In other instances, the insert ring is rigid.

In some embodiments, the adjustable ostomy wafer systems, devices and methods disclosed herein comprise an internal adhesive layer that at least partially covers the body-facing surface of the adjustable layer. In some instances, the adjustable layer comprises an adhesive agent. In some instances, the adjustable layer provides a barrier or seal against effluent, ensuring effluent flows only through the effluent opening. In some instances, the height of the insert ring may be modulated by the user before or during use. The adjustable ostomy wafer system of any preceding claim, comprising a coupling component that couples the ostomy wafer to an ostomy pouch.

In some instances, the coupling component of the adjustable ostomy wafer systems, devices and methods disclosed herein mechanically couples the ostomy wafer to the ostomy pouch. In yet other instances, the coupling component adhesively couples the ostomy wafer to the ostomy pouch. In still other instances, the coupling component can be attached to the ostomy pouch and subsequently separated without damage to the ostomy pouch or the coupling component.

In some instances, disclosed herein are ostomy devices and methods, the ostomy devices and methods comprising the adjustable ostomy wafer systems, devices and methods disclosed herein and an ostomy pouch. In some embodiments, the ostomy wafer is permanently attached to the ostomy pouch. In still other embodiments, the ostomy wafer and ostomy pouch are configured such that the effluent opening is not sealed to an ostomy pouch opening until after the insert ring is pressed against the non-body-facing side of the adjustable layer and the ostomy wafer is applied to the stoma. In yet other instances, the ostomy wafer and ostomy pouch are provided as separate pieces before use.

In still other instances, the ostomy methods, devices and systems disclosed herein comprise contacting a flush stoma or a retracted stoma with the ostomy wafer. In some instances, the insert ring is pressed or capable of being pressed into the adjustable layer to provide or increase convexity of the adjustable layer. In yet instances, the insert ring is retractable or capable of being retracted from the adjustable layer after pressing to decrease convexity.

In some embodiments, disclosed herein are kits comprising an ostomy wafer comprising an adjustable layer, with an effluent opening through which effluent flows; and a plurality of insert rings capable of providing or increasing convexity of the adjustable layer when the insert ring is pressed against the non-body-facing side of the adjustable layer, wherein a first insert ring and a second insert ring of the plurality of insert rings differ in an aspect selected from diameter, rigidity, height, and a combination thereof. In some instances, at least one insert ring comprises a groove that engages a portion of the adjustable layer. In other instances, the first insert ring and the second insert ring each comprise at least one groove. In yet other instances, the first insert ring and the second insert ring comprise a different number of grooves.

In yet other instances, the kits disclosed herein further comprises an ostomy pouch, wherein the ostomy pouch is capable of coupling to a coupling component of the ostomy wafer. In still other embodiments, the ostomy pouch and the ostomy wafer are provided as separate components before use. In other embodiments, the ostomy pouch and the ostomy wafer are connected before use, but the effluent opening and non-body-facing side of the ostomy wafer is exposed before use.

DETAILED DESCRIPTION

Figure 1:
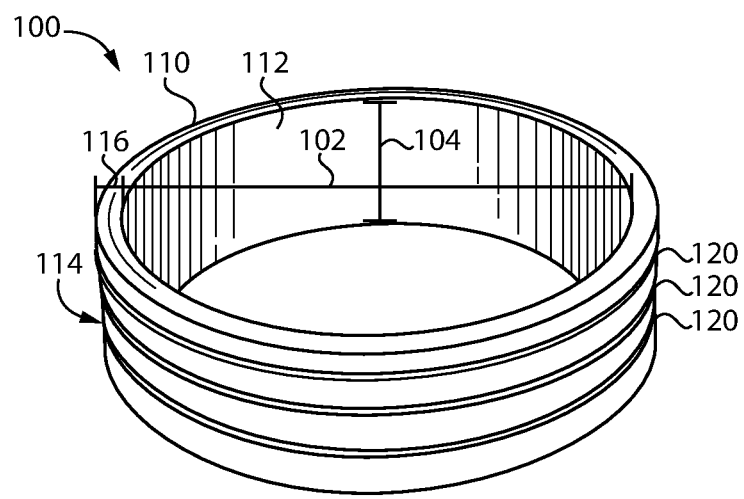
FIG. 1 depicts an embodiment of an insert ring with grooves.

Current convex ostomy wafer products are inadequate, affording inflexible options for an ostomate that may require change over time. To address this need, ostomy wafers that provide different levels of convexity are disclosed herein. Thus, the ostomy wafers disclosed herein may be referred to as adjustable ostomy wafers or convex adjustable wafers, due to the custom, adjustable convexity that they afford. Custom convexity is achieved with an insert ring, which is generally more rigid than the ostomy wafer itself. Insert rings disclosed herein generally have a structure or feature that allows it to engage the ostomy wafer, thereby maintaining its position in the ostomy wafer. In addition to providing user-customized convexity, the insert ring provides increased support or stability at the base of the stoma relative to existing ostomy wafers (without insert rings). This increased support or stability provides the benefit of a more secure fit, while the surrounding adjustable layer in contact with the body ensures user comfort.

Provided herein are devices, systems and kits that comprise adjustable ostomy wafers. The adjustable ostomy wafers disclosed herein are accompanied by insert rings which are used as an instrument to vary convexity of the wafers. In some instances, adjustable ostomy wafers disclosed herein comprise a mouldable, stretchable, or flexible layer, referred to as an adjustable layer herein. In some instances, at least a portion of the adjustable ostomy wafers disclosed herein is mouldable or comprises a mouldable component.

In some embodiments, adjustable layers of the ostomy wafers disclosed herein have an adhesive surface on a body-facing side. In some embodiments, the adjustable layer comprises a first adhesive surface and an external layer (radially surrounding or overlapping the adjustable layer) comprises a second adhesive surface. The first adhesive surface and the second adhesive surface may have different properties suitable to different regions of the stoma and surrounding skin. In some embodiments, the adjustable layer does not have an adhesive surface and the external layer (radially surrounding or overlapping the adjustable layer) comprises an adhesive surface on a body-facing side of the external layer.

Generally, the ostomy wafers disclosed herein possess no convexity or a minimum amount of convexity before use, and an increased amount of convexity, relative to the minimum amount, during use. The ostomy wafers disclosed herein are designed to be adjustable to fit a variety of stoma depths, sizes, and shapes.

Provided herein are methods for using insert rings disclosed herein with existing ostomy wafers. Further provided herein are methods for modifying existing ostomy wafers to function with insert rings disclosed herein. For example, existing moldable wafers may be modified with a wafer insert that can engage the insert ring. The wafer insert may be a substantially two-dimensional wafer insert, simply providing a rim around the effluent opening of the wafer that is relatively more rigid than the ostomy wafer and capable of engaging the insert ring. The two-dimensional wafer insert may be desirable to a user who wants to wear form-fitting clothing. Alternatively, the wafer insert may be a three-dimensional wafer insert, also referred to herein as a convex insert. The convex insert may providing additional structure for engaging the insert ring, thereby stabilizing the insert ring in the ostomy wafer and providing greater security. This may be desirable to a user who is more physically active.

Certain Terminologies

Unless defined otherwise, all technical and scientific terms used herein have the same meaning as is commonly understood by one of skill in the art to which the claimed subject matter belongs. It is to be understood that the foregoing general description and the following examples are exemplary and explanatory only and are not restrictive of any subject matter claimed. In this application, the use of the singular includes the plural unless specifically stated otherwise. It must be noted that, as used in the specification and the appended claims, the singular forms "a," "an," and "the" include plural referents unless the context clearly dictates otherwise. In this application, the use of "or" means "and/or" unless stated otherwise. Furthermore, use of the term "including" as well as other forms, such as "include," "includes," and "included," is not limiting.

As used herein, ranges and amounts can be expressed as "about" a particular value or range. About also includes the exact amount. For example, "about 5 cm" means "about 5 cm" and also "5 cm." Generally, the term "about" includes an amount that would be expected to be within experimental error. The term "about" includes values that are within 10% less to 10% greater of the value provided. For example, "about 50%" means "between 45% and 55%." Also, by way of example, "about 30" means "between 27 and 33."

The section headings used herein are for organizational purposes only and are not to be construed as limiting the subject matter described.

As used herein, the terms "individual(s)," "subject(s)," and "patient(s)" mean any mammal. In some embodiments, the mammal is a human. In some embodiments, the mammal is a non-human.

For the purposes of the present application, the term "stoma" refers to an opening in the body. Generally the stoma is a surgical opening in the torso of the body. In some instances, the term "stoma" also refers to internal tissue, organs or portions thereof that are exposed by the opening. By way of non-limiting example, internal tissue may be selected from colon, ileum, small intestine, large intestine, jejunum, and duodenum, and combinations thereof. The internal tissue may be an end or a loop of a small or large intestine.

Unless specified otherwise, the term "flush/retracted skin" refers to any skin surrounding the opening, whether it be external skin or peristomal skin, or a combination thereof.

For the purposes of the present application, the term "external skin" refers to skin near the stoma, but generally not in contact with internal tissues or effluent. As used herein, the term "peristomal skin" refers to skin in contact with internal tissues or likely to contact effluent.

The term "effluent" refers to any internal fluids produced by an ostomate that may be secreted from the stoma or that exit the stoma.

As used herein, the term "ostomate" refers to a subject that may have use of the ostomy wafers disclosed herein. While ostomate usually refers to a subject with a surgical opening, as used herein, "ostomate" may refer to a subject who has a stoma, regardless of whether the stoma was created by surgery or other means.

The ostomy wafers disclosed herein are described for use with a gastrointestinal stoma, but could be used in other contexts as well. The ostomy wafers disclosed herein may be used for managing a stoma created by an esophagostomy, a gastrostomy, a cholecystectomy, a choledochostomy, a cecostomy, a colostomy, a duodenostomy, an ileostomy, a jejunostomy, an appendicostomy, a tracheostomy, a urostomy, urostomy, a nephrostomy, an ureterostomy, or a vesicostomy.

As used herein, the term "wafer" may be used interchangeably with the terms "adapter," "adjustable wafer," "convex wafer," "three-dimensional mouldable adapter," "ostomy wafer," or "adjustable convex wafer." In some instances, where it is noted, the term "wafer" may refer collectively to all layers, e.g., the external layer and the adjustable layer, of the ostomy wafer. Unless otherwise specified, these terms may be used interchangeably.

The ostomy wafers disclosed herein may be used with additional ostomy wafers including, but not limited to, a shunt, a catheter, a cap, and a plug.

Adjustable Wafer System

Figure 2:
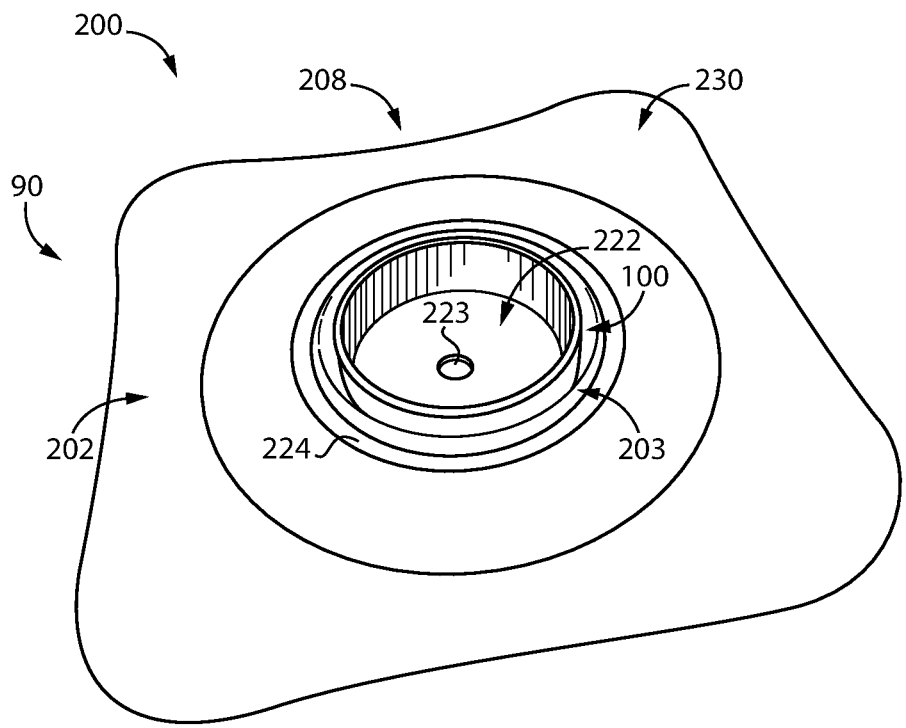
FIG. 2 depicts an embodiment of an unactuated adjustable wafer from the pouch facing side of the wafer.
Figure 3:
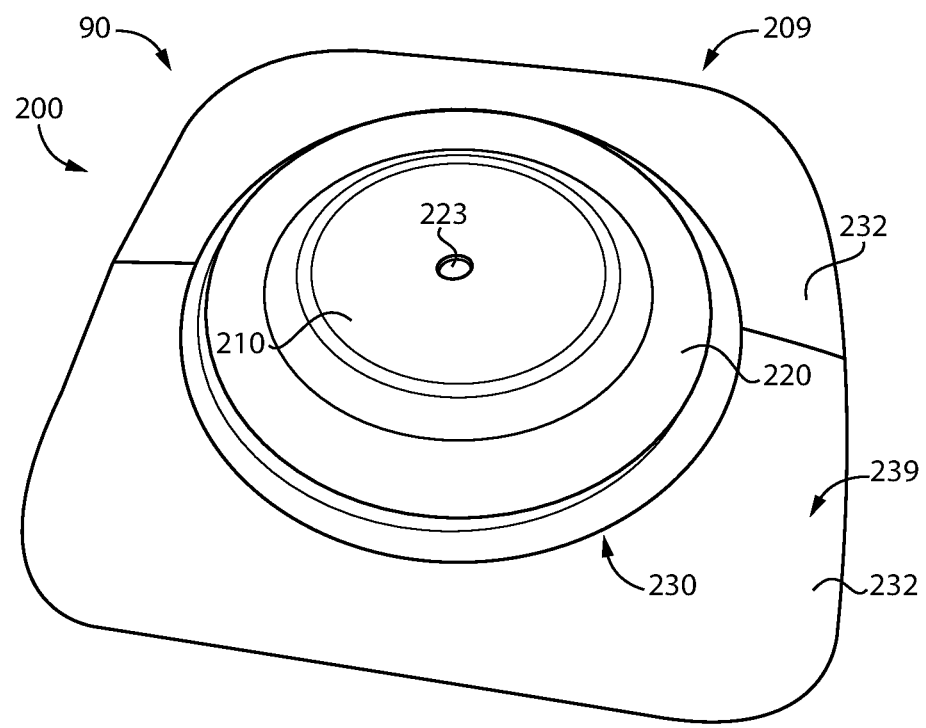
FIG. 3 depicts an embodiment of an adjustable wafer with minimal convexity, viewed from the stoma facing side of the wafer.
Figure 4:
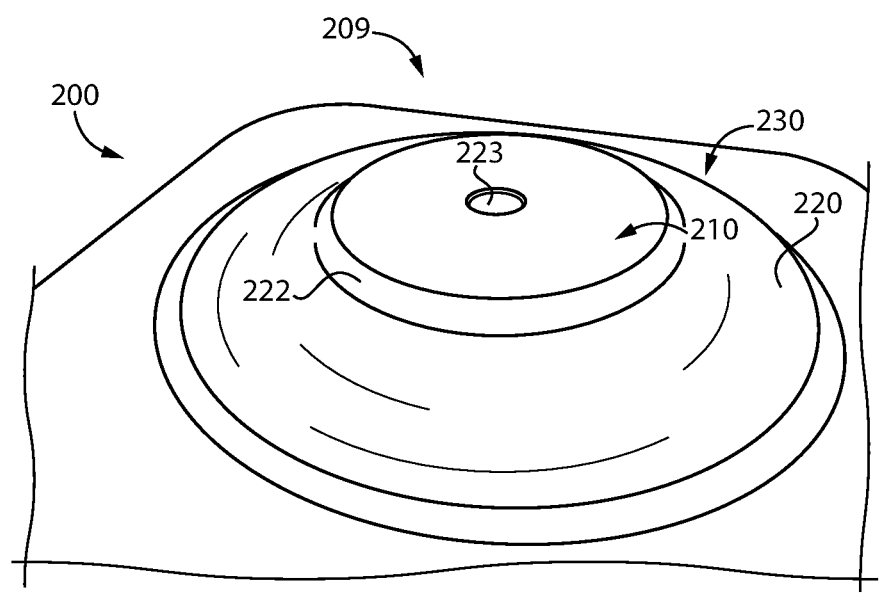
FIG. 4 depicts an embodiment of an adjustable wafer with medium convexity, viewed from the stoma facing side of the wafer.
Figure 5:
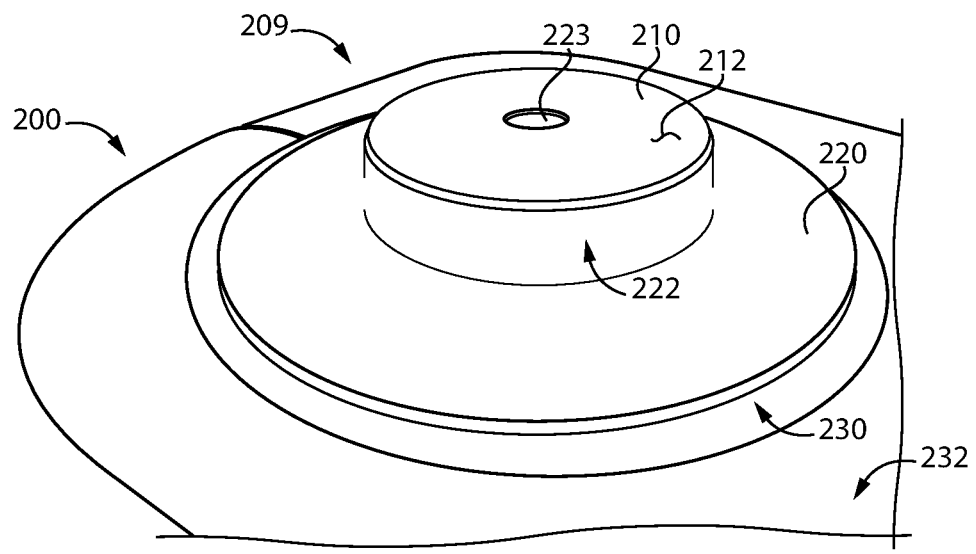
FIG. 5 depicts an embodiment of an adjustable wafer with maximal convexity, viewed from the stoma facing side of the wafer.
Figure 6:
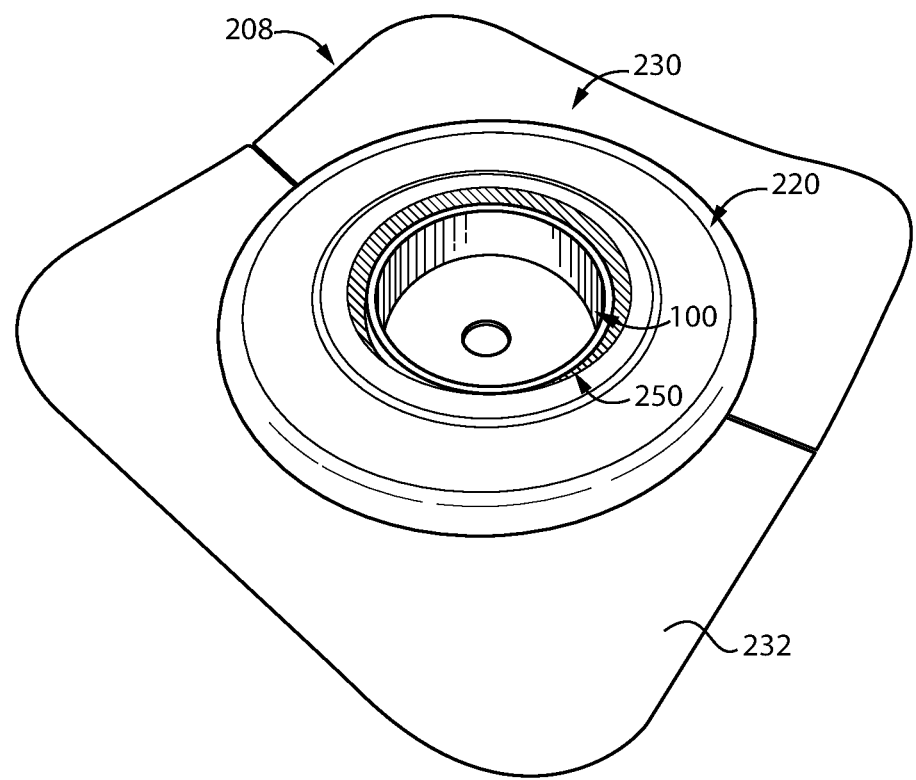
FIG. 6 depicts an embodiment of a fully actuated adjustable wafer with maximal convexity, viewed from the pouch facing side of the wafer.

Provided herein are adjustable ostomy wafer systems 90 and kits that comprise adjustable ostomy wafers 200 and insert rings 100 disclosed herein. Certain adjustable ostomy wafers 200 disclosed herein comprise an adjustable layer 220 capable of customized convexity when the insert ring 100 is pressed against the adjustable layer 220 or a region thereof. Further provided herein are methods that comprise the use of adjustable ostomy wafers 200 and insert rings 100 disclosed herein. In some embodiments, insert rings 100 disclosed herein comprise at least one groove 120 as shown in FIG. 1. The at least one groove 120 may allow the insert ring 100 to engage the ostomy wafer 200 at varying positions or depths of ostomy wafer convexity. In some embodiments, the ostomy wafer system 90 may be provided to the ostomate in an unactuated conformation, as seen in FIG. 2. In some instances, the insert ring 100 is provided together with the wafer 200 with a minimum degree of convexity as shown in FIG. 3. A user of the ostomy wafer 200 may depress the ring 100 into the adjustable layer 220 to obtain a medium degree of convexity, as shown in FIG. 4. The user may then further depress the insert ring 100 to obtain a higher degree of convexity, as shown in FIGS. 5 and 6.

Provided herein are ostomy wafers 200 that comprise an adjustable layer 220, wherein the adjustable layer 220 is a mouldable adjustable layer. In some instances, the mouldable adjustable layers 220 disclosed herein are entirely mouldable. In some instances, the mouldable adjustable layers 220 disclosed herein are partially mouldable. In some instances, the mouldable adjustable layer 220 is mouldable in a region proximal to the effluent opening 223, but not at the outer edge of the mouldable adjustable layer 220. The mouldable adjustable layers 220 disclosed herein may comprise a three dimensional mouldable technology which, due to its ability to conform to the stoma and surrounding skin, increases patient comfort, peace of mind and quality of life. The mouldable adjustable layer 220 can be manipulated and molded by the insert rings 100 disclosed herein and/or a user's finger(s). The mouldable adjustable layers 220 disclosed herein may be adjusted to fit a variety of stomaeristomal skin shapes, conditions and sizes. The ostomy wafers 200 disclosed herein aim to provide a better fit for ostomates, molding not simply to the stoma, but also molding to irregular skin contours and folds.

Provided herein are adjustable ostomy wafers systems 90 that comprise: a mouldable adjustable layer 220 and an insert ring 100 positioned inside the mouldable adjustable layer 220, wherein the mouldable adjustable layer 220 and the insert ring 100 comprise openings through which effluent flows. In some embodiments, the wafer 200 comprises an external layer 230 having an adhesive body-contacting side 239. The inner region of the external adhesive layer body-facing side 239 may at least partially overlap with the mouldable adjustable layer 220 to connect these two layers and form a base 202 (of the adjustable wafer). The inner circumference of the external layer 230 may be rigid and formed to engage a groove 120 of an insert ring 100. The insert ring 100, shown in FIG. 1 and FIG. 7, may be provided with the adjustable wafer 200, for example in a kit or system 90. FIG. 2 depicts the external layer 230 on the non-body-facing side 208 of the adjustable wafer 200. The insert ring 100 is visible from the non-body-facing side 208 where it is accessible to the ostomate or caregiver. FIG. 3 depicts the body-facing side 209 of the adjustable wafer 200 and the mouldable adjustable layer 220. Release liners 232 in FIG. 3 are in place before use shielding the adhesive of the external layer 230 until use.

The convexity and mouldability of ostomy wafers 200 disclosed herein may provide an effective barrier that molds to a stoma and to irregular skin contours and folds. The ostomy wafers 200 disclosed herein are designed to adapt to the stoma, providing an improved seal against effluent on the skin, and minimizing skin irritation and breakdown. Minimizing the risk of leakage helps an ostomy patient feel more confident in his or her ability to manage his or her stoma. As compared to current devices, the ostomy wafers 200 provided in the present application reduce the risk of leakages, reduce the risk of consequent infections, and reduce user distress and discomfort.

The ostomy wafers 200 disclosed herein generally provide a primary interface seal that contacts the base of the ileum or perimeter of the stoma, to lessen the likelihood of effluent seeping underneath skin barriers of the adjustable wafers 200 disclosed herein. In some instances, the adjustable layer 220 forms the primary interface seal. In some instances, the internal layer 210 forms the primary interface seal. In some instances, the adjustable layer 220 and the internal layer 210 together form the primary interface seal. In some instances, an additional layer forms the primary interface seal. In some instances, the ostomy wafers 200 disclosed herein, or at least one layer thereof, may be molded to conform to the surrounding peristomal skin, improving the seal. In some embodiments, the ostomy wafers 200 disclosed herein may have an adhesive sealed design, conferring flexibility and malleability in order to adapt to the external environment of the stoma. The ostomy wafers 200 disclosed herein may be mouldable to stomas, without needing physical modification (e.g., cutting, tearing) to achieve an appropriate and effective fit. As a result, the user is more confident in the ostomy wafers 200 of the present application, less likely to experience embarrassing leakage, less likely to develop infection, and less likely to experience leakage-related skin damage, as compared to use with current ostomy wafers.

The application of ostomy skin barrier products can be a time consuming process for many patients. As a result of the ostomy wafers 200 disclosed herein being adaptable to each individual, the application time is minimized. In some embodiments, the ostomy wafers 200 disclosed herein have the potential to eliminate the need for sealing accessories such as paste and adhesive gaskets which can be costly, time-consuming, and messy. Easier application means its use will be easier to teach for nurses and easier to learn for patients. The ostomy wafers 200 disclosed herein are described for use with a gastrointestinal stoma, but could be used in other contexts as well where a convex shape or form is needed.

While the ostomy wafers 200 disclosed herein are especially advantageous for the management of flush or retracted stomas, the ostomy wafers 200 disclosed herein may be used for protruding stomas as well. For example, the protruding stoma may be buried between skin folds or buried in a skin crease, thereby creating an effective recessed or retracted stoma. Generally, a protruding stoma is characterized by internal tissue (e.g., ileum) protruding from a surgical opening beyond the surface of surrounding external skin. A flush stoma may be described as having protruding internal tissue, but the protruding tissue is surrounded by skin such that the distal end of the protruding internal tissue is flush with or surrounding external and/or peristomal skin. Thus, the protruding tissue does not extend beyond the surface of the surrounding skin. A retracted stoma may be characterized by an absence of protruding internal tissue. In the case of a retracted stoma, the internal tissue does not protrude beyond the perimeter of the stoma or the skin surrounding the stoma. One of the benefits of the ostomy wafers 200 disclosed herein is the ability to fit a range of stoma environments and topographies, thereby eliminating the need for ostomates to purchase different products as their stoma environment changes.

In the case of a flush stoma, the ostomy wafers 200 disclosed herein can be pressed into or against the stoma resulting in the effluent opening of the adjustable layer 220 surrounding the internal tissue, with the peristomal skin at least partially surrounding and/or burying the adjustable layer 220. In the case of a retracted stoma, the adjustable layer 220 may be pressed into or against the stoma to be at least partially surrounded by or buried in the peristomal skin without the opening of the adjustable layer 220 surrounding any internal tissue. In some cases, the insert ring 100 is pressed against or in to the adjustable layer 220 before the ostomy wafer is applied to the stoma. In some instances, the insert ring 100 is further pressed against or in to the adjustable layer 220 after the ostomy wafer is applied to the stoma. In some cases, the insert ring 100 is pressed against or in to the adjustable layer 220 before the ostomy wafer 200 is applied to the stoma. In order to press the insert ring 100 against or in to the adjustable layer 220 after the ostomy wafer 200 is applied to the stoma, the ostomy wafer 200 may have a hole, ridge, or ring for the user's fingers to engage and to apply a counter pressure to the pressure being applied on the insert ring 100.

Provided herein are adjustable ostomy wafer systems 90 wherein the insert rings 100 are used with novel or existing ostomy wafers that have been designed or modified to engage the insert rings 100 disclosed herein. The ostomy wafers 200 disclosed herein may comprise a layer that is initially flat, a flexible layer, a multi-layered laminate, a tapered thickness layer, or combinations thereof. However, the ostomy wafers 200 disclosed herein generally have a layer or a portion thereof that is adjustable, stretchable, flexible or mouldable so that ostomy wafer convexity may be provided or increased by pressure with an insert ring 100 disclosed herein. The ostomy wafers 200 disclosed herein generally allow at least for minimal convexity (e.g., at least ⅛ inch). In certain embodiments, the ostomy wafers 200 disclosed herein additionally or alternatively provide a small degree of convexity (e.g., height of actuated ostomy wafer is ⅛ inch to ½ inch). In certain embodiments, the ostomy wafers 200 disclosed herein additionally or alternatively provide a large degree of convexity (e.g., height of actuated ostomy wafer is 0.5 inches to 1.5 inches).

Users of ostomy devices often complain about the discomfort of convex products. However, a certain amount of rigidity may be necessary to create the seal at the base of retracted stomas. In some embodiments, the devices disclosed herein allow for increased comfort through a wafer perimeter that is more flexible than that of standard wafers while maintaining the rigidity via the insert ring 100 nearest the base of the stoma where it is needed. In some embodiments, the flexibility of the wafer 200 may decrease from the outer perimeter of the wafer towards the opening of the wafer. In some embodiments, the convexity (e.g., depth) is limited by the extensibility of the adjustable layer 220. For example, the adjustable layer may comprise a laminated adhesive. Durahesive Trilaminate is limited to about a depth of 0.5 inches. Varying convexities of the wafers are disclosed herein.

In some embodiments, the ostomy wafers 200 disclosed herein have the potential to eliminate the need for sealing accessories such as paste and seals. In some embodiments, sealing accessories are used with the ostomy wafers 200 disclosed herein.

Insert Ring

Provided herein are ostomy wafer systems and kits that comprise insert rings 100 disclosed herein. The insert rings 100 are used in conjunction with adjustable layers 220 of ostomy wafers 200 disclosed herein to provide varying levels of convexity to the ostomy wafers 200. The ostomy wafer 200 with insert ring 100 may be provided to the ostomate separately. The ostomy wafer system 90 may be provided to the ostomate wherein the ostomy wafer 200 and the insert ring 100 are provided to the ostomate already engaged in an unactuated conformation with minimal convexity, for example as seen in FIGS. 2 and 3. If more convexity is needed, then the user would simply depress the insert ring 100 deeper into the adjustable layer 220, stretching, extending, deepening or moulding the adjustable layer 220 to the desired level. For example, when more convexity is desired, a device user may depress the insert ring 100 into a mouldable adjustable layer 220 disclosed herein, deepening the mouldable adjustable layer 220 to a medium convexity, as shown in FIG. 4, or maximal (fully actuated) convexity, as shown in FIGS. 5 and 6.

The insert rings 100 disclosed herein may take on many shapes. A non-limiting example of a cylindrical insert ring 100 is depicted in FIG. 1 with a diameter 102 and a height 104 perpendicular to the diameter 102. However, the insert rings 100 disclosed herein may be cone-shaped, funnel-shaped, or tapered. In other words, the diameter 102 may vary along the height 104 of the insert ring 100. In some embodiments, an opening of the insert ring 100 is circular. In some embodiments, an opening of the insert ring 100 is elliptical. In some embodiments, an opening of the insert ring 100 is irregular. In some embodiments, the end of the insert ring 100 that is in direct contact with the user's fingers (not in direct contact with the adjustable layer 220), comprises a lip, edge, or tab for assisting in the application of the insert ring 100. In this way, insert rings 100 of various shapes may allow for the insert rings 100 to accommodate different stoma shapes and sizes, while reducing device bulk and/or increasing ease of manipulating the ring 100. The latter would be especially advantageous for those users with reduced dexterity.

The insert ring 100 may be defined by an annular wall 110 with an inner surface 112 and an outer surface 114. The insert ring wall 110 may have a uniform thickness 116. The insert ring wall 110 may have varying thickness 116. In certain embodiments, at least one portion of the wall 110 may have a thickness 116 of about 0.1 cm. In certain embodiments, at least one portion of the wall 110 may have a thickness 116 of about 0.2 cm. In certain embodiments, at least one portion of the wall 110 may have a thickness 116 of about 0.3 cm. In certain embodiments, at least one portion of the wall 110 may have a thickness 116 of about 0.4 cm. In certain embodiments, at least one portion of the wall 110 may have a thickness 116 of about 0.5 cm. In some embodiments, the wall 110 of the insert ring 100 at the end of the insert ring 100 that is in direct contact with the user's fingers is thicker in order to receive pressure from fingers without fingers slipping off the ring 100. The latter would be especially advantageous for those users with reduced dexterity or poor eyesight.

The insert rings 100 disclosed herein may function as a single structural element. For instance, no additional parts, structures, components, or tools are necessary to employ the insert ring 100. No additional parts, structures, components, or tools are necessary to increase the convexity of the adjustable layer other than the user's fingers and the insert ring 100 itself.

The insert ring 100 may have a diameter 102 of about 2 cm to about 5 cm. The insert ring 100 may have a diameter 102 of about 2 cm to about 4.5 cm. The insert ring 100 may have a diameter 102 of about 2 cm to about 4 cm. The insert ring 100 may have a diameter 102 of about 2 cm to about 3.5 cm. The insert ring 100 may have a diameter 102 of about 2 cm to about 3 cm.

The insert ring 100 may have a height 104 (perpendicular to the diameter 102 of the insert ring 100) between about 1 cm and about 5 cm. The insert ring 100 may have a height 104 between about 1 cm and about 4.5 cm. The insert ring 100 may have a height 104 between about 1 cm and about 4 cm. The insert ring 100 may have a height 104 between about 1 cm and about 3.5 cm. The insert ring 100 may have a height 104 between about 1 cm and about 3 cm. The insert ring 100 may have a height 104 between about 1 cm and about 2.5 cm. The insert ring 100 may have a height 104 between about 1 cm and about 2 cm.

The insert ring 100 may comprise a ceramic material. The insert ring 100 may comprise a metal. The insert ring 100 may comprise a hard plastic. The insert ring 100 may consist essentially of a ceramic material. The insert ring 100 may consist essentially of a metal. The insert ring 100 may consist essentially of a hard plastic. The insert ring 100 may consist of a ceramic material. The insert ring 100 may consist of a metal. The insert ring 100 may consist of a hard plastic. The insert ring 100 may comprise or consist of any material that provides the insert ring 100 with a rigidity sufficient to receive force from a user and transfer that force into increasing the convexity of the adjustable layer 220.

In some embodiments, the shape of the base 202 of the wafer 200 may help to prevent the insert ring 100 from being pushed back as the inner diameter of the adjustable layer 220 would tend to decrease when force is applied to the insert ring 100 to form the convex shape. In some embodiments, the wafer 200 is a minimal convex adjustable wafer. In some embodiments, the wafer 200 is a medium convex adjustable wafer. In some embodiments, the wafer 200 is a maximal convex adjustable wafer. The shape of the wafer 200 would prevent retraction as it would cause the inner diameter to decrease when force is applied to the insert ring 100 from the adhesive side.

Figure 7:
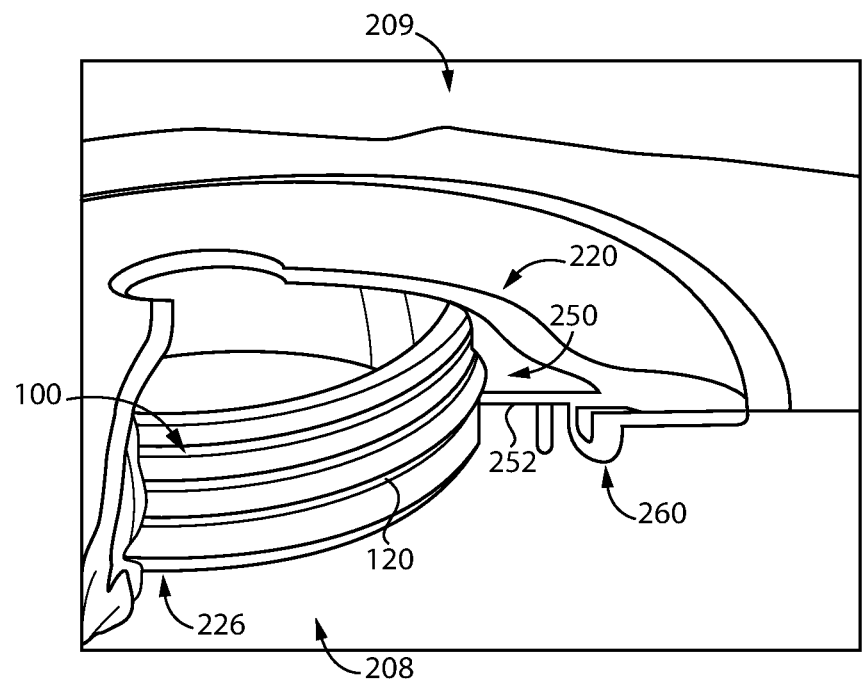
FIG. 7 depicts an embodiment of an adjustable wafer, showing a side view cross section with a convex insert than engages an insert ring.

The insert ring 100 may have a groove 120. The insert ring 100 may have a plurality of grooves 120 as shown in FIG. 1. The ostomy wafer 200 may have convex insert 250 as shown in FIG. 7 that allows a groove 120 of the insert ring 100 to be set (temporarily or permanently) into a position. The insert ring 100 with a plurality of grooves 120 may allow for setting or locking the ring 100 into varying positions (e.g., an extended position), maintaining varying depths of convexity, as needed. Additionally or alternatively, the insert ring 100 may have grooves 120 that engage a rigid structure present at the inner circumference of the external layer, adjustable layer or combination thereof. Alternatively or additionally, the insert ring 100 may have a rigid structure or locking tab that engages one or more grooves of the adjustable wafer 200. A first groove 120 and a second groove 120 may be spaced by a distance of about 0.2 cm to about 1 cm. The first groove 120 and the second groove 120 may be spaced by a distance of about 0.2 cm to about 0.8 cm. The first groove 120 and the second groove 120 may be spaced by a distance of about 0.2 cm to about 0.5 cm. The first groove 120 and the second groove 120 may be spaced by a distance of about 0.2 cm to about 0.4 cm. The first groove 120 and the second groove 120 may be spaced by a distance of about 0.3 cm to about 0.5 cm.

In the case of a flush stoma, the insert ring 100 may be pressed into or against the stoma so that the internal tissue passes through the opening 223 of the adjustable layer 220, resulting in the adjustable wafer 200 surrounding the internal tissue, and peristomal skin at least partially surrounding/burying the adjustable wafer 200. In the case of a retracted stoma, the insert ring 100 may be pressed into the adjustable layer 220 so that the adjustable wafer 200 is at least partially surrounded by or buried in the peristomal skin without surrounding any internal tissue, or without the opening 223 surrounding any internal tissue.

In some embodiments, the insert ring 100 provides a depth to a convex space 226 of the adjustable layer 220. The depth of the convex space 226 may be about 0.5 cm to about 5 cm. The depth of the convex space 226 may be about 0.5 cm to about 4 cm. The depth of the convex space 226 may be about 0.5 cm to about 3 cm. The depth of the convex space 226 may be about 1 cm to about 5 cm. The depth of the convex space 226 may be about 1.5 cm to about 5 cm. The depth of the convex space 226 may be about 2 cm to about 5 cm. The depth of the convex space 226 may be about 2.5 cm to about 5 cm.

In some embodiments, the insert ring 100 has an inner diameter 102 to cover stoma openings that have a diameter of about a half inch to about two inches. In some embodiments, the opening of the insert ring 100 is circular. In some embodiments, the opening of the insert ring 100 is irregular. In some embodiments, the opening of the insert ring 100 is oval. In some embodiments, the insert ring 100 is adapted for a larger stoma, which may benefit from oval shape convexity.

Locking Tabs and Convex Inserts

Provided herein are devices, systems, and kits that comprise an adjustable ostomy wafer 200 and an insert ring 100, wherein the adjustable ostomy wafer 200 comprises a ring-engaging structure that engages the insert ring 100, holding the insert ring 100 in place. The ring-engaging structure generally engages a groove 120 of the insert ring 100. In some instances, the ring-engaging structure is provided separately from the adjustable ostomy wafer. In some instances, the ring-engaging structure is attached, connected or an integral part of the adjustable ostomy wafer 200. The ring-engaging structure may be a rim or ridge located around the circumference of the effluent opening 223, with a rigidity that is greater than the adjustable layer 220. The ring-engaging structure may be a convex insert 250. A cut-away view of an exemplary convex insert 250 is shown in FIG. 7. In some instances, the convex insert 250 forms an entire ring. In some instances, the convex insert 250 is only present in regions around the wafer 200. In some instances, the convex insert 250 comprises a single ridge to engage the groove(s) 120 of the insert ring 100. In some instances, the convex insert 250 has multiple ridges to engage the groove(s) 120 of the insert ring 100.

In some instances the convex insert 250 provides one or more ridges complementary to the groove(s) 120 of the insert ring 100, such that the insert ring 100 may be screwed into or twisted into the convex insert 250. Conversely, if the ostomate decides he or she would like to decrease the convexity once the ostomy wafer 200 is applied, the ostomate may unscrew or untwist the insert ring 100, thereby retracting the insert ring 100 and decreasing convexity of the adjustable ostomy wafer 200.

In some instances, the ring-engaging structure is a locking tab 252 to engage the insert ring 100. In some instances, the adjustable ostomy wafer 200 comprises a plurality of locking tabs 252. The locking tab 252 may be permanently connected to the adjustable wafer 200 (e.g., cannot be removed without damage to the wafer). The locking tab 252 may be separate from the wafer 200, but capable of being connected to the wafer 200. The locking tab 252 may be connected, either permanently or temporarily, to the external layer 230. The locking tab 252 may be connected, either permanently or temporarily, to the adjustable layer 220. The locking tab 252 may be connected, either permanently or temporarily, to the base of the wafer 200 formed by a combination of the external layer 230 and the adjustable layer 220. The locking tab 252 may be connected, either permanently or temporarily, to the inner circumference of the external layer 230 or an inner region of the external layer 230 that is rigid and formed to engage a groove 120 of an insert ring 100. The locking tab 252 may be connected, either permanently or temporarily, to the inner circumference 203 of the wafer base 202 or an inner region of the wafer base 202 that is rigid and formed to engage a groove 120 of an insert ring 100.

The locking tab 252 may have any appropriate shape and size for engaging the insert ring 100. The locking tab 252 may be inflexible, rigid or hard. The locking tab 252 may be made of a material with a physical property similar to hard plastic. The locking tab 252 may comprise a material with a physical property similar to hard plastic. The locking tab 252 may be made of a hard plastic material. The locking tab 252 may comprise a hard plastic material.

Adhesives

Disclosed herein are adjustable ostomy wafer systems to be used with ostomy devices, methods and kits, wherein the adjustable ostomy wafer systems may comprise adhesives or uses thereof. The general term "adhesive," also referred to as "adhesive agent," as used herein, refers to layers, fabrics, strips, laminates, barriers, gels, pastes, hydrocolloids, and glues that may be used to promote adherence of the adjustable wafer system to the ostomate and/or promote a seal between the adjustable wafer system and the ostomate, thereby preventing undesirable leakage of effluent. The adhesive may comprise a sealing substance that promotes a seal between the adjustable wafer system and the stoma/ostomate, thereby preventing effluent leakage. The adjustable wafer systems disclosed herein generally comprise an adhesive. However, it is not necessary for the adjustable wafer systems to comprise an adhesive.

In certain embodiments, the adjustable wafers 200 disclosed herein comprise a moldable adhesive. In certain embodiments, the adjustable wafers 200 disclosed herein comprise a swellable adhesive. In certain embodiments, the adjustable wafers 200 disclosed herein comprise an adhesive that swells when exposed to stomal output. In certain embodiments, the adjustable wafers 200 disclosed herein comprise an adhesive that when exposed to stomal output seals around the stoma. In certain embodiments, the adhesive is hydrocolloid and/or silicone-based. In certain embodiments, the adhesive is Durahesive or Stomahesive. In certain embodiments, the adjustable wafers 200 disclosed herein comprise Durahesive Trilaminate. In certain embodiments, a thicker layer of Durahesive in the Trilaminate is used for the body contact layer. In certain embodiments, the thicker layer of Durahesive in the Trilaminate provides the seal at the base of the stoma. In certain embodiments, a thinner layer of Durahesive in the Trilaminate provides the attachment of the adhesive wafer 200 to the convex component. In certain embodiments, an inner film layer provides support to the portion of the adhesive at the inner diameter of the convex component. Without this film the adhesive in this area may break up during use. In certain embodiments, the inner film helps to hold the adhesive together during deployment of the insert ring 100, while being extensible to facilitate the deployment of the insert ring 100. In some embodiments, the insert ring 100 can be used for other adhesive laminations, but these factors may need to be considered.

Alternatively, or additionally, kits and methods may comprise an adhesive (e.g., an adhesive paste), or use thereof, that can be applied to the adjustable wafer system 200, effectively eliminating gaps between the stoma and the adjustable wafer system 200. Adhesives may also be used to promote adherence of an ostomy pouch 310 to the adjustable wafer system 90. The adhesives disclosed herein ideally provide adhesion for a variety of skin conditions, as well as provide security and comfort for the patient. To ensure the skin barrier adheres well to moist/dry skin, hydrocolloids may be used. The adhesives, such as barriers, seals, strips, laminates or fabrics, may comprise a release liner that is to be removed before use. In other instances, the adhesives may not be provided with a release liner. Rather, the adhesive quality of the adhesive may be present only when the adhesive makes contact with a liquid, gel, effluent, skin, heat, or combinations thereof. The adhesives may have an adhering, sealing, or molding quality that is activated and/or promoted by heat, and/or contact with effluent. Such adhesives are well known in the field of ostomy care.

The ostomy wafers 200 disclosed herein may comprise a 3D mouldable technology that can be used to further improve the fit between the adjustable ostomy wafer and stomas. For example, ConvaTec Mouldable Technology (CMT), which improves the fit between skin barriers and stomas, can be used in addition to the adjustable wafer systems 90 disclosed herein. For example, Durahesive technology used in CMT helps to protect the skin from caustic effluent. Durahesive uses the effluent as an advantage, swelling or "turtlenecking" when coming in contact with liquid effluent, thereby improving the seal around the stoma. This adaptability to expand and contract around the stoma means that the barrier will remain snug and secure during wear time. Ensuring a good seal around the stoma minimizes the risk of effluent leaking under the skin barrier; reducing this risk of leakage helps prevent the development of peristomal skin complications.

The adjustable wafer system disclosed herein and components thereof may comprise an adhesive selected from various adhesives, including, but not limited to Durahesive/film/Durahesive Trilaminate. The formulation of these adhesives may be altered to increase further the product's appeal (e.g. comfort, flexibility, size, breathability, etc.). To improve the elasticity of the adhesive, an addition of a material (e.g., styrene-isoprene-styrene (SIS) rubber) could be added. Oils could also be added to enhance the pliability and tack.

The adhesives disclosed herein may comprise a mucoadhesive. The mucoadhesive may be particularly help for maintaining sufficient adhesion under wet conditions. The mucoadhesive of certain embodiments comprises a polymer with functional groups that provide adhesion to skin and stoma. The functional groups are selected from a group consisting of thiols, acids and their salts, iminothiolanes, thioalkylamidines, catechols, amino acids, dihydroxy substituted aromatic groups, and combinations thereof. The polymer is a biocompatible polymer made from natural or synthetic polymer selected from a group consisting of polyacrylates, polyakylmethacrylates, polyphenylmethacrylate, polyanhydrides, styrenic block copolymers, polyamides, polyesters, polyvinyl ethers, polyvinyl esters, sulfonated polymers, polyolefins, silicones, polyvinylpyrrolidones, polyvinylacetate and its copolymers, polyvinyl alcohol, polyurethanes, polyethers, copolymers of maleic anhydride, polysaccharides, polypeptides, gelatin, alginates, gums, starch, chitosan, pectin, and combinations thereof. The mucoadhesive may further contain other components such as hydrophobic polymers, hydrophilic polymers, amphiphilic polymers, tackifiers, resins, plasticizers, hydrocolloids, inorganic and organic particulate fillers, antioxidants, and combinations thereof.

The adhesives may comprise a pressure sensitive adhesive comprising one or more amphiphilic copolymers of polydimethylsiloxane, wherein the copolymer is prepared using a polydimethylsiloxane or polymethylhydrogensiloxane macroinitiator and at least one reactive hydrophilic or amphiphilic monomer, oligomer, macromer and combinations thereof. The reactive hydrophilic or amphiphilic monomer may be selected from a group consisting of N-vinyl caprolactams, vinyl esters, vinyl ethers, unsaturated acids or anhydrides and their salts, acrylates, methacrylates, acrylamides, methacrylamides, N-alkyl acrylamides, cyanate esters, hydroxy-alkyl acrylamides, glycidyl esters, glycidyl ethers, allyl monomers, and combinations thereof.

Wafer Layers

Provided herein are ostomy devices and systems comprising wafers disclosed herein. The ostomy wafers disclosed herein (e.g., the ostomy wafer 200) may comprise multiple layers. These layers may include an external layer 230, an adjustable layer 220, and/or an internal layer 210 disclosed herein. The layers may function as molds, adhesives, seals, or skin barriers.

The ostomy wafers 200 disclosed herein may comprise an external layer 230, also referred to herein as an "external adhesive layer," in some embodiments. The external layer 230 may be the outermost (most distal to the ostomate) layer of the ostomy wafer 200. The external layer 230 may be a layer that does not extend into the stoma or internally beyond the stoma when applied to the ostomate. In certain embodiments, the external layer 230 may consist of a single layer. In certain embodiments, the external layer 230 may comprise a multilayer or multi-laminate material or multiple layers of material. In certain embodiments, the external layer 230 may comprise Trilam (SH/DH). The Trilam may comprise a Stomahesive seal or a Durahesive seal. The external layer 230 may be described as a collar or flange to the adjustable layer 220 of the ostomy wafer.

The ostomy wafers 200 disclosed herein may comprise an adjustable layer 220. The adjustable layer 220 may be made of a material that allows for its deformation relative to its initial shape. For example, the adjustable layer 220 may be flexible, stretchable, mouldable, or extendable. Unless specified otherwise, any one of the adjustable layers 220 disclosed herein may be a mouldable adjustable layer. The mouldable adjustable layer 220 may be entirely mouldable or partially mouldable. At least a portion of the mouldable adjustable layers 220 disclosed herein are mouldable. The portion may be proximal to the effluent opening 212. The portion may be an area of the mouldable adjustable layer 220 in contact with the stoma.

The adjustable layer 220 may comprise a skin barrier. The skin barrier may comprise a mouldable adhesive. The mouldable adhesive may be flexible or pliable. The skin barrier may be ring-shaped. The adjustable layer 220 may comprise an adhesive. The adjustable layer 220 may comprise a stoma adhesive that adheres the adjustable layer to flush/retracted skin of the flush/retracted stoma, thereby securing and/or sealing the adjustable wafer system 90 to the ostomate. The adjustable layer 220 or skin barrier may comprise a stoma adhesive. The stoma adhesive may provide a barrier or seal against effluent, ensuring effluent flows only through the opening 223 of the adjustable layer 220.

Preferably, the skin barrier is mouldable, breathable, and/or moisture-absorbing. By way of non-limiting example, the skin barrier may be selected as a Stomahesive Seal (ConvaTec) and/or a Brava Mouldable Ring (Coloplast). These skin barriers are designed to fill in cavities/folds in the intact skin around the stoma, helping to protect the underlying skin from contact with bodily fluids. These are typically made from pectin-based, hydrocolloid-type ingredients, although composition varies by brand.

The adjustable layer 220 may be described as relatively cylindrical, funnel-shaped or bowl-shaped, with a mouth/rim that is in contact with the external layer 230. The opening 223 of the adjustable layer 220 through which effluent flows is generally positioned at/near the base 222 of the bowl, opposite the mouth/rim 224. The adjustable layer 220 should have appropriate dimensions for positioning into, around or against a flush or retracted stoma. For instance, with regards to the flush stoma, the opening of the adjustable layer 220 would fit around the internal tissue with the convex sides of the "bowl" contacting the peristomal skin that rises around or surrounds the internal tissue, and the "rim" of the "bowl" would not extend or would minimally extend beyond the surface of the surrounding skin. In the instance of a retracted stoma, the adjustable layer 220 would not necessarily have to be especially deep, but ideally would be wide enough to leave little or no space between the peristomal skin and the rim or sides of the bowl (adjustable layer 220). Thus, the depth of the "bowl" (adjustable layer 220) may be between about half of a centimeter and about ten centimeters. The width of the bowl (adjustable layer 220) may be between about two centimeters and about ten centimeters. The mouldable adjustable layer 220, as well as additional components of the adjustable wafer systems 90 disclosed herein, may be manufactured by use of compression molds. Application of heat is also a possibility for molding an adhesive layer or component of the ostomy wafers 200 disclosed herein.

Certain embodiments provided herein relate to wafer systems 90 consisting essentially of an adjustable layer 220 disclosed herein and an insert ring 100 disclosed herein. The adjustable layer 220 may consist of a single layer. The single layer may be an adjustable layer 220 disclosed herein. The adjustable layer 220 may comprise multiple materials laminated together. The adjustable layer 220 may comprise a multi-laminate material. The adjustable layer 220 may comprise a material selected from Stomahesive seal.

The external adhesive layer 230 and the adjustable layer 220 are generally concentric, while the external adhesive layer 230 and adjustable layer 220 may at least partially overlap. Typically, the outer diameter of the external adhesive layer 230 is greater than the outer diameter of the adjustable layer 220. In some instances, the external adhesive layer 230 surrounds the adjustable layer 220 circumferentially. In some instances, the external adhesive layer 230 and the adjustable layer 220 may not necessarily overlap. In some instances, the external adhesive layer 230 has a flat ring shape and the adjustable layer 220 has a three-dimensional ring shape during use.

The adjustable wafer 200 may comprise one or more additional layers. The one or more additional layers may comprise, for example, an additional adhesive layer. The one or more additional layers may also be concentric with the adjustable layer 220. For example, ostomy wafers disclosed herein may comprise an external adhesive layer 230 concentrically surrounding an adjustable layer 220, wherein the adjustable layer 220 is substantially and directly surrounded by the external adhesive layer 230. Alternatively, ostomy wafers 200 disclosed herein may comprise an external adhesive layer 230 concentrically surrounding an adjustable layer 220, wherein the adjustable layer 220 is separated from the external adhesive layer 230 by an additional layer. The additional layer may comprise a barrier, seal or adhesive not provided by the adjustable layer 220 that provides further protection against leakage. This would be especially advantageous where the external adhesive layer 230 is primarily designed to adhere to external skin, but not provide much of a barrier against effluent.

The adjustable wafers 200 disclosed herein may comprise an internal layer 210. The internal layer 210 may at least partially cover the body-facing surface of the mouldable adjustable layer 220, and comprises a stoma adhesive 212 on a stoma-facing side 209 of the internal layer 210. The stoma adhesive 212 adheres the internal layer 210 to flush/retracted skin of the flush/retracted stoma, thereby additionally securing the adjustable wafer 200 to the ostomate. The internal layer 210 may be positioned on the convex surface 222 of the adjustable layer 220 so that the internal layer 210 contacts peristomal skin. The internal layer 210 may comprise Stomahesive seal. The internal layer 210 may comprise Stomahesive paste.

The adjustable wafers systems 90 disclosed herein may comprise one or more additional layers. The one or more additional layers may comprise at least one adhesive. The one or more additional layers may not necessarily comprise adhesive. The one or more additional layers may comprise a material selected from adhesive, laminate, foam, gel, rubber, fabric, plastic, and combinations thereof. The one or more additional layers may contribute to the flexibility or mouldable character of the disclosed adjustable wafer systems.

The adjustable wafer systems may further comprise a flange or collar attached to the external layer 230, wherein the flange or collar comprises additional skin adhesive for further securing the adjustable wafer system 90 to the ostomate and/or sealing the adjustable wafer systems 90 to the ostomate, thereby preventing leakage. In addition, there are numerous methods for providing a successful fit and/or seal when applying a flange to the stoma; a common method is by applying an adhesive substance around the stoma. For instance, a paste is a highly effective sealant and protective skin barrier; the paste may be used between the base of the ileum or perimeter of the stoma and the opening of the wafer/baseplate as filler for skin folds, uneven skin surfaces and scars. Another method is by using silicone gel to fill uneven skin surfaces; once the gel is applied directly around the stoma the ostomate then applies a wafer/baseplate directly onto the gel. The gel will then cure underneath the wafer/baseplate during normal wear time. Examples of pastes and gel include, but are not limited to, ConvaTec's Stomahesive paste.

The adjustable wafer systems 90 disclosed herein may further comprise a coupling component 260 that couples or adheres the adjustable wafer system 90 to, for example, an ostomy pouch 310 or an ostomy cap. The coupling component 260 may be attached to the wafer 200, wherein the wafer 200 comprises an external layer 230 and an adjustable layer 220. The coupling component 260 may be an additional layer of the wafer 200. The coupling component 260 may mechanically connect the adjustable wafer system 90 to the ostomy pouch. The coupling component 260 may connect the adjustable wafer systems 90 disclosed herein to the ostomy pouch 310 via an adhesive, the adhesive being provided by the ostomy pouch 310 or component thereof, and/or by the coupling component or by an additional product (e.g., glue, paste). Alternatively, the adjustable wafer systems 90 disclosed herein may not necessarily comprise a coupling component 260. Instead, the adjustable wafer systems 90 may contact the pouch 310 directly or be integrated into an ostomy device 300 (such as a wafer directly connected to an ostomy pouch, bag or cap) or may contact a coupling component on the pouch 310, bag, or cap.

Ostomy Devices

Figure 8:
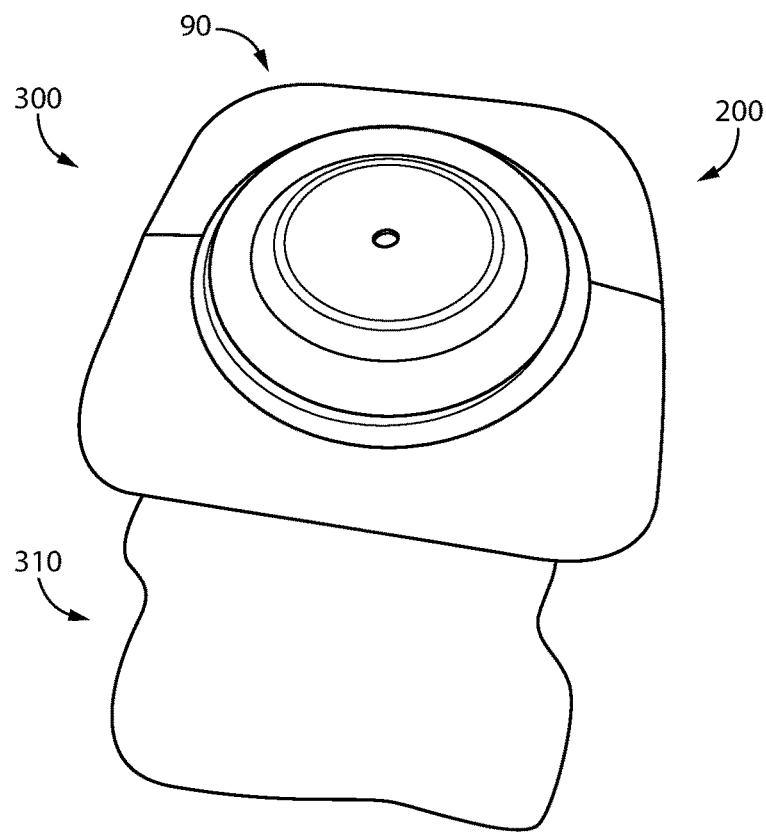
FIG. 8 depicts an embodiment of an ostomy device including an adjustable wafer and an ostomy pouch.

With additional reference to FIG. 8, further disclosed herein are ostomy systems or devices 300 that comprise an ostomy pouch 310, bag or cap and any one of the adjustable ostomy wafers 200 disclosed herein. The ostomy device 300 may comprise one or more coupling components on the ostomy pouch 310 and/or adjustable ostomy wafer 200 for connecting the ostomy pouch 300 and adjustable ostomy wafer 200 in an operative state. The coupling component may comprise a limited motion connection between the adjustable wafer system 90 and the ostomy pouch 310 that permits relative displacement between (i) substantially the entire adjustable wafer system 90 and (ii) the entrance aperture of the ostomy pouch 310, the limited motion connection guiding said relative displacement along a limited motion locus, between (a) an operative position and an access position; and (b) a fixation coupling for fixing the adjustable wafer systems 90 disclosed herein and the ostomy pouch 310 when in the operative position.

In certain embodiments, the devices 300 disclosed herein comprise two or more separate pieces. In certain embodiments, the devices 300 disclosed herein comprise an ostomy wafer 200 disclosed herein and a pouch 310, wherein the ostomy wafer 200 and pouch 310 are separate. In certain embodiments, the devices 300 disclosed herein comprise an ostomy wafer 200 and a pouch 310, wherein the ostomy wafer 200 and pouch 310 are separable before and/or after use. In certain embodiments, the pouch 310 and/or ostomy wafer 200 are referred to as a two-piece device. In certain embodiments, the pouch 310 and/or ostomy wafer 200 are provided with a coupling mechanism. In certain embodiments, the coupling mechanism is selected from a flange coupling and an adhesive coupling. In certain embodiments, the pouch 310 and the ostomy wafer 200 are permanently connected. In certain embodiments, the device 300 is referred to as a one-piece device or system. In certain embodiments, the pouch 310 and ostomy wafer 200 are permanently connected via an adhesive component and/or a mechanical component. In certain embodiments, the pouch 310 and ostomy wafer 200 are not separated without damaging the pouch 310 and/or ostomy wafer 200.

In the operative position, the adjustable wafer system 90 is superposed around the entrance aperture of the ostomy pouch 310, and an adaptable region of the adjustable ostomy wafer 200 is shrouded by, for example, an ostomy pouch 310 on the non-body-facing side 208. The access position provides access to the adaptable region from the non-body-facing side 208.

Such an arrangement can guide alignment of the adjustable ostomy wafer 200 and the ostomy pouch 310 to the operative position, making such alignment much easier for elderly, non-dexterous, or visually impaired persons. At the same time, the limited motion coupling permits relative displacement of substantially the entire adjustable ostomy wafer 200 with respect to the entrance aperture, allowing access for adapting the adjustable ostomy wafer 200 to the size and/or shape of the user's stoma. The limited motion connection may comprise an articulating link, the articulation defining the locus of limited motion.

The ostomy device 300 may be a one-piece ostomy device to enhance access to the adjustable wafer system 90, while avoiding problems of a wholly or partly immovable adjustable wafer system as in the prior art. The adjustable wafer systems 90 disclosed herein may be permanently attached to the ostomy pouch 310 directly, or permanently attached to the coupling component, wherein the coupling component is permanently attached to the ostomy pouch 310. As used herein the term "permanently attached" (or like phrases) means that the pieces are attached so strongly that they cannot be separated without breakage or damage that prevents reattachment without additional equipment. The ability to relatively displace the entire adjustable wafer system 90 with respect to the entrance aperture of the ostomy pouch 310 may permit easier adaptation of the adjustable wafer system 90 (whether by forming, cutting or shaping the stomal aperture, or by fitting and/or shaping a separate sealing member at the stomal aperture).

The ostomy device 300 disclosed herein may also be a two-piece ostomy device to facilitate easier alignment of the components, without significantly reducing ease of access for adapting the adjustable wafer system 90 to the size and/or shape of stoma, nor detracting from the ability to position the body-fitment on the body before fixing the appliance in the operative position with respect to the body fitment. The limited motion connection and the coupling component may comprise releasable coupling portions.

The adjustable wafer systems 90 disclosed herein may work well for two-piece and one-piece ostomy devices. The insert ring 100 may be actuated through the pouch film.

Methods of Use

Provided herein are methods of using the adjustable ostomy wafers and ostomy devices disclosed herein. The methods may comprise providing or increasing a convexity of an adjustable layer 220 to the adjustable ostomy wafer 200. Providing or increasing the convexity may comprise pressing an insert ring 100 disclosed herein into or against the adjustable layer 220. Providing or increasing the convexity may comprise screwing, twisting, or pushing an insert ring 100 disclosed herein into or against the adjustable layer 220. The methods may comprise contacting a stoma of a subject with an adjustable ostomy wafer 200 disclosed herein, wherein a convexity of the adjustable ostomy wafer 200 has been adjusted with an insert ring 100 disclosed herein. The methods may comprise contacting a stoma of a subject with an adjustable ostomy wafer 200 disclosed herein, and subsequently adjusting a convexity of an adjustable layer 220 of the wafer with an insert ring 100 disclosed herein. The methods disclosed herein may comprise retracting the insert ring 100 from the adjustable layer 220 to decrease convexity. Retracting may comprise pulling, twisting, or unscrewing an insert ring 100 from the adjustable ostomy wafer. Retracting may comprise disengaging a groove 120 of an insert ring 100 from the adjustable ostomy wafer 200 or portion thereof. Retracting may comprise disengaging a groove 120 of an insert ring from a locking tab 252 disclosed herein.

The methods may further comprise contacting the adjustable ostomy wafer 200 with an ostomy pouch 310 or plug that fills the opening(s) of the adjustable ostomy wafer 200. The methods may further comprise contacting the flush/retracted stoma or the adjustable ostomy wafer 200 with an adhering substance that promotes adherence of the adjustable ostomy wafer 200 to the ostomate. The methods may further comprise contacting the flush/retracted stoma or the adjustable ostomy wafer 200 with an additional adhesive besides the adhesive(s) that is a component of the adjustable ostomy wafer 200. The methods may comprise applying heat for molding the adjustable ostomy wafer 200 or promoting the adherent property of the additional adhesive.

Kits

Figure 9:
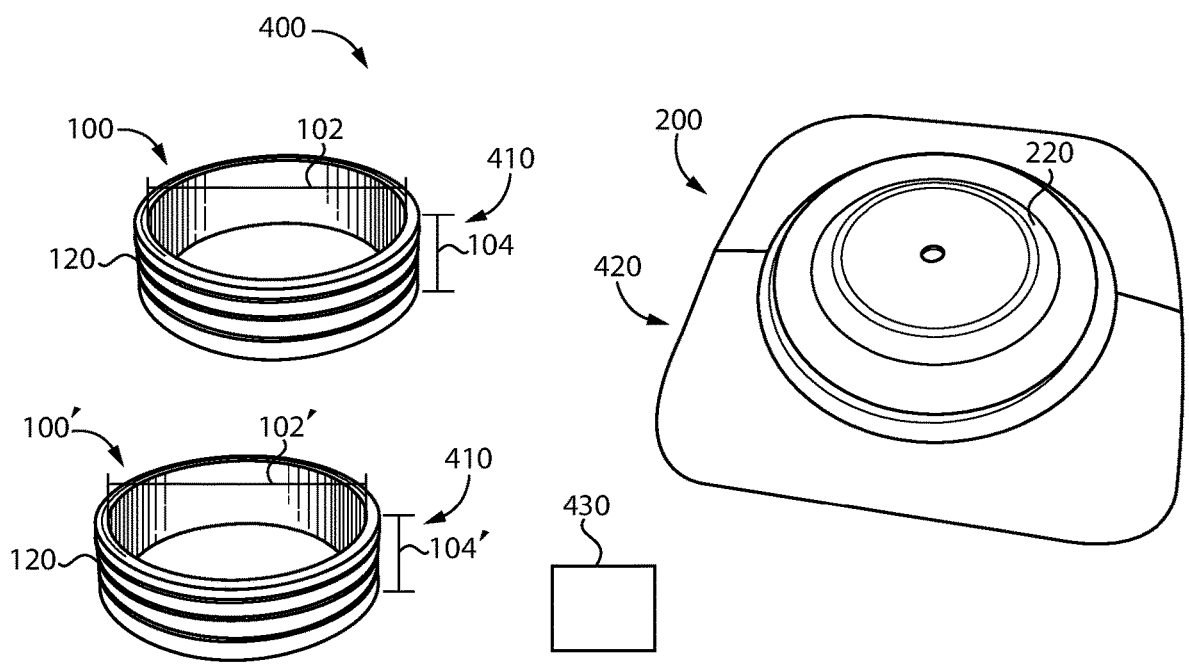
FIG. 9 depicts an embodiment of a kit including a plurality of insert rings and an ostomy wafer.

With additional reference to FIG. 9, certain embodiments of the present application relate to a kit 400 including a plurality of insert rings 410 and an ostomy wafer 420. The insert rings 410 may be provided along the lines of the above-described insert ring 100, and may include a first insert ring 100 and a second insert ring 100'. The ostomy wafer 420 may be provided along the lines of the ostomy wafers 200 described herein. In certain embodiments, a kit 400 comprises: an ostomy wafer 420, 200 comprising an adjustable layer 220, with an effluent opening 223 through which effluent flows; and a plurality of insert rings 410 capable of providing or increasing convexity of the adjustable layer 220 when the insert ring 100/100' is pressed against the non-body-facing side 208 of the adjustable layer 220, wherein a first insert ring 100 and a second insert ring 100' of the plurality of insert rings 410 differ in an aspect selected from diameter, rigidity, height, and a combination thereof. In some embodiments, at least one insert ring 100 of the plurality of insert rings 410 comprises a groove 120 that engages a portion of the adjustable layer 220. In some embodiments, the first insert ring 100 and the second insert ring 100' each comprise at least one groove 120. In some embodiments, the first insert ring 100 and the second insert ring 100' comprise a different number of grooves 120.

The kit 400 may further comprise a kit component 430 selected from an ostomy pouch (e.g., the above-described ostomy pouch 310), an adhesive seal, an adhesive barrier, an adhesive strip, an adhesive fabric, an adhesive paste, and combinations thereof. The ostomy pouch 310 may be capable of coupling to a coupling component 260 of the ostomy wafer 200.

In some embodiments, the kit 400 comprises a plurality of insert rings 410 wherein a first insert ring 100 has a first diameter 102 and a second insert ring 100' has a second diameter 102'. In some embodiments the first diameter 102 and the second diameter 102' are the same. In some embodiments, the first diameter 102 and the second diameter 102' are different. In some embodiments, the kit 400 comprises a single insert ring 100 with a plurality of peel away layers or a peel away layer with a guide so as to adjust the insert ring 100 to the size of the stoma opening. In some embodiments, the kit 400 comprises a plurality of insert rings 410 that are nested and removed as needed.

In some embodiments, the kit 400 comprises a plurality of insert rings 410 wherein a first insert ring 100 has a first height 104 and a second insert ring 100 has a second height 104'. In some embodiments, the first height 104 and the second height 104' are the same. In some embodiments, the first height 104 and the second height 104' are different.

In some embodiments, the kits comprise a plurality of insert rings 410 wherein a first opening of a first insert ring 100 has a first opening diameter 102 and a second opening of a second insert ring 100' has a second opening diameter 102'. In some embodiments, the first opening diameter 102 and the second opening diameter 102' are the same. In some embodiments, the first opening diameter 102 and the second opening diameter 102' are different.

EXAMPLES

Example 1: Application of an Adjustable Ostomy Wafer with Adjustable Convexity to a Retracted Stoma; Adjusting Convexity Prior to Application Hands and skin surrounding the stoma are clean, dry and free from any solvent or oily substances before applying the ostomy system. The adjustable wafer 200 has an external (adhesive) layer 230 with a body-facing side 209 outer region that adheres to skin around the stoma. The inner region of the external adhesive layer 230 body-facing side 209 partially overlaps with an adjustable layer 220 to connect these two layers 220, 230 and form the base (of the adjustable wafer). The inner circumference of the external layer 230 is rigid and formed to engage a groove 120 of an insert ring 100. The insert ring 100, shown in FIG. 1 and FIG. 7 is provided with the adjustable wafer 200, for example in a kit. FIG. 2 depicts the non-body-facing side 208 of the adjustable wafer 200. The insert ring 100 is visible from the non-body-facing side 208 where it is accessible to the ostomate or caregiver. FIG. 3 depicts the body-facing side 209 of the adjustable wafer 200. Release liners 232 are in place before use shielding the adhesive of the external layer 230 until use.

The insert ring 100 is depressed into the adjustable layer and into the stoma opening, increasing the convexity of the adjustable layer. The user must pull back on the base 202 with fingers while pushing the insert ring 100 down with thumbs. The insert ring 100 is depressed into the adjustable layer 220 to meet the depth of the stoma. The adjustable ring 100 engages the inner circumference of the external layer 230, maintaining the convexity of the adjustable wafer 200. The user desires more convexity and depresses the insert ring 100 into the adjustable layer 220 further, engaging the next groove 120 in the insert ring 100, thereby maintaining a higher degree of convexity for the adjustable wafer 200. Immediately before use, the release liners 232 are removed. The body-facing side 209 and opening of the adjustable layer 220 is centered over the stoma. The adjustable wafer 200 is pressed against the stoma and surrounding skin. The external layer 230 adheres to skin surrounding the stoma. By compressing the skin barrier around the stoma the adhesive molds around the stoma, providing an effective seal. The adjustable layer 220, which is made of a material that constitutes a skin barrier, is molded to the stoma opening shape and size, without needing scissors to adapt the ostomy system. The skin barrier is applied against the skin around the stoma for thirty seconds, allowing the barrier to adapt or mold to the environment. Coverage and comfort are tested with ISO 8670-2 testing, Ink testing and/or Flex testing (e.g. Zwick U.T.M).

Example 2: Application of a Mouldable Wafer with Adjustable Convexity to a Refracted Stoma; Adjusting Convexity During and After Application Hands and skin surrounding the stoma are clean, dry and free from any solvent or oily substances before applying the ostomy system. The adjustable wafer has an external (adhesive) layer 230 with a body-facing side 209 outer region that adheres to skin around the stoma. The inner region of the external adhesive layer 230 body-facing side 209 partially overlaps with an adjustable layer 220 to connect these two layers, 220, 230 forming a wafer base 202. The inner circumference of the external layer 230 or wafer base 202 is rigid and formed to engage a groove 120 of an insert ring 100. The insert ring 100, shown in FIG. 1 and FIG. 7, is provided with the adjustable wafer 200, for example in a kit. FIG. 2 depicts the non-body-facing side 208 of the adjustable wafer 200. The insert ring 100 is visible from the non-body-facing side 208 where it is accessible to the ostomate or caregiver. FIG. 3 depicts the body-facing side 209 of the adjustable wafer 200. Release liners 232 are in place before use, thereby shielding the adhesive of the external layer 230 until use. Immediately before use, the release liners 232 are removed.

The body-facing side 209 and opening 223 of the adjustable layer 220 is centered over the stoma. The adjustable wafer 200 is pressed against the stoma and surrounding skin. The external layer 230 adheres to skin surrounding the stoma. The insert ring 100 is depressed into the adjustable layer 220 and into the stoma opening, increasing the convexity of the adjustable layer 220. The insert ring 100 is depressed into the adjustable layer 220 to meet the depth of the stoma. The adjustable ring 100 engages the inner circumference of the external layer 230, maintaining the convexity of the adjustable wafer 200. The user desires more convexity and depresses the insert ring 100 into the adjustable layer 220 further, engaging the next groove 120 in the insert ring 100, thereby maintaining a higher degree of convexity for the adjustable wafer 200. The adjustable layer 220, which is made of a material that constitutes a skin barrier, is molded to the stoma opening shape and size, without needing scissors to adapt the ostomy system. The skin barrier is applied against the skin around the stoma for thirty seconds, allowing the barrier to adapt/mold to the environment. Coverage and comfort are tested with ISO 8670-2 testing, Ink testing and/or Flex testing (e.g. Zwick U.T.M).

Example 3—Application of a Mouldable Wafer with Adjustable Convexity to a Refracted Stoma; Adjusting and Maintaining Convexity Without Engagement of Adjustable Ring Insert Grooves Hands and skin surrounding the stoma are clean, dry and free from any solvent or oily substances before applying the ostomy system 90. The adjustable wafer 200 has an external (adhesive) layer 230 with a body-facing side 209 outer region that adheres to skin around the stoma. The inner region of the external adhesive layer 230 body-facing side 209 partially overlaps with an adjustable layer 220 to connect these two layers. The insert ring 100, shown in FIG. 1 and FIG. 7, is provided with the adjustable wafer 200, for example in a kit. FIG. 2 depicts the non-body-facing side 208 of the adjustable wafer 200. The insert ring 100 is visible from the non-body-facing side 208, where it is accessible to the ostomate or caregiver. FIG. 3 depicts the body-facing side 209 of the adjustable wafer 200. Release liners 232 are in place before use shielding the adhesive of the external layer 230 until use. Immediately before use, the release liners 232 are removed.

The body-facing side 209 and opening of the adjustable layer 220 is centered over the stoma. The adjustable wafer 200 is pressed against the stoma and surrounding skin. The external layer 230 adheres to skin surrounding the stoma. The insert ring 100 is depressed into the adjustable layer 220 and into the stoma opening, increasing the convexity of the adjustable layer 220. The insert ring 100 is depressed into the adjustable layer to meet the depth of the stoma. Once the desired depth is met, the insert ring 100 is removed and the adjustable layer 220 maintains its convexity due to the nature of the material of which the adjustable layer 220 is formed. Alternatively, the insert ring 100 remains depressed into the adjustable layer 220. The adjustable layer 220, which is made of a material that constitutes a skin barrier, is molded to the stoma opening shape and size, without needing scissors to adapt the ostomy system 90. The skin barrier is applied against the skin around the stoma for thirty seconds, allowing the barrier to adapt/mold to the environment. Coverage and comfort are tested with ISO 8670-2 testing, Ink testing and/or Flex testing (e.g., Zwick U.T.M).

Certain embodiments of the present application relate to an adjustable ostomy wafer system comprising: a. an ostomy wafer comprising an adjustable layer, with an effluent opening through which effluent flows; and b. an insert ring capable of providing or increasing convexity of the adjustable layer when the insert ring is pressed against the non-body-facing side of the adjustable layer.

In certain embodiments, the adjustable ostomy wafer system further comprises an external adhesive layer extending beyond an outer edge of the adjustable layer, wherein the external adhesive layer has an adhesive body-facing side.

In certain embodiments, the adjustable layer holds the insert ring in place during use to maintain the convexity in the adjustable layer.

In certain embodiments, the insert ring comprises a groove that engages a portion of the adjustable layer.

In certain embodiments, the groove engages an edge of the adjustable layer located proximal to the effluent opening, thereby securing and maintaining a position of the insert ring in the adjustable layer.

In certain embodiments, the adjustable ostomy wafer system further comprises a convex insert, wherein the groove engages the convex insert, thereby securing and maintaining a position of the insert ring in the adjustable layer.

In certain embodiments, at least a portion of the convex insert that engages the groove is more rigid than the adjustable layer or a portion thereof.

In certain embodiments, the adjustable ostomy wafer system further comprises at least one locking tab that engages the groove of the insert ring, maintaining a position of the insert ring in the adjustable layer.

In certain embodiments, the insert ring comprises a plurality of grooves, wherein each of the grooves corresponds to a different level of convexity of the adjustable layer.

In certain embodiments, the convexity of the adjustable layer is varied between a minimal convexity of about ⅛ inch and a maximal convexity of about 1 inch.

In certain embodiments, the convexity of the adjustable layer is varied between a minimal convexity of about ½ inch and a maximal convexity of about 1 inch.

In certain embodiments, the adjustable ostomy wafer system further comprises an internal adhesive layer that at least partially covers the body-facing surface of the adjustable layer.

In certain embodiments, the adjustable layer comprises an adhesive agent.

In certain embodiments, the adjustable layer provides a barrier or seal against effluent, ensuring effluent flows only through the effluent opening.

In certain embodiments, the height of the insert ring may be modulated by the user.

In certain embodiments, the insert ring is flexible.

In certain embodiments, the insert ring is rigid.

In certain embodiments, the adjustable ostomy wafer system further comprises a coupling component that couples the ostomy wafer to an ostomy pouch.

In certain embodiments, the coupling component mechanically couples the ostomy wafer to the ostomy pouch.

In certain embodiments, the coupling component adhesively couples the ostomy wafer to the ostomy pouch.

In certain embodiments, the coupling component can be attached to the ostomy pouch and subsequently separated without damage to the ostomy pouch or the coupling component.

Certain embodiments relate to an ostomy device comprising the adjustable ostomy wafer system and an ostomy pouch.

In certain embodiments, the ostomy wafer is permanently attached to the ostomy pouch.

In certain embodiments, the ostomy wafer and ostomy pouch are configured such that the effluent opening is not sealed to an ostomy pouch opening until after the insert ring is pressed against the non-body-facing side of the adjustable layer and the ostomy wafer is applied to the stoma.

In certain embodiments, the ostomy wafer and ostomy pouch are provided as separate pieces before use.

Certain embodiments relate to a method of using the adjustable ostomy wafer system or the ostomy device, the method comprising contacting a flush stoma or a retracted stoma with the ostomy wafer.

In certain embodiments, the method further comprises pressing the insert ring into the adjustable layer to provide or increase convexity of the adjustable layer.

In certain embodiments, the method further comprises retracting the insert ring from the adjustable layer after pressing to decrease convexity.

Certain embodiments of the present application relate to a kit comprising: a. an ostomy wafer comprising an adjustable layer, with an effluent opening through which effluent flows; and b. a plurality of insert rings capable of providing or increasing convexity of the adjustable layer when the insert ring is pressed against the non-body-facing side of the adjustable layer, wherein a first insert ring and a second insert ring of the plurality of insert rings differ in an aspect selected from diameter, rigidity, height, and a combination thereof.

In certain embodiments, at least one insert ring comprises a groove that engages a portion of the adjustable layer.

In certain embodiments, the first insert ring and the second insert ring each comprise at least one groove.

In certain embodiments, the first insert ring and the second insert ring comprise a different number of grooves.

In certain embodiments, the kit further comprises an ostomy pouch, wherein the ostomy pouch is capable of coupling to a coupling component of the ostomy wafer.

In certain embodiments, the ostomy pouch and the ostomy wafer are provided as separate components before use.

In certain embodiments, the ostomy pouch and the ostomy wafer are connected before use, but the effluent opening and non-body-facing side of the ostomy wafer is exposed before use.

What is claimed is:

1. An adjustable ostomy wafer system comprising:
   a. an ostomy wafer comprising an adjustable layer, with an effluent opening through which effluent flows, wherein the adjustable layer has a body-facing side and a non-body-facing side; and
   b. an insert ring capable of providing or increasing convexity of the adjustable layer when the insert ring is pressed against the non-body-facing side of the adjustable layer, wherein the insert ring is capable of providing or increasing convexity of the adjustable layer when translated relative to the ostomy wafer without rotation relative to the ostomy wafer.

2. The adjustable ostomy wafer system of claim 1, further comprising an external adhesive layer extending beyond an outer edge of the adjustable layer, wherein the external adhesive layer has an adhesive body-facing side.

3. The adjustable ostomy wafer system of claim 1, wherein the adjustable layer holds the insert ring in place during use to maintain the convexity in the adjustable layer.

4. The adjustable ostomy wafer system of claim 1, wherein the insert ring comprises a groove that engages a portion of the adjustable layer.

5. The adjustable ostomy wafer system of claim 4, wherein the groove engages an edge of the adjustable layer located proximal to the effluent opening, thereby securing and maintaining a position of the insert ring in the adjustable layer.

6. The adjustable ostomy wafer system of claim 4, further comprising a convex insert, wherein the groove engages the convex insert, thereby securing and maintaining a position of the insert ring in the adjustable layer.

7. The adjustable ostomy wafer system of claim 6, wherein at least a portion of the convex insert that engages the groove is more rigid than the adjustable layer or a portion thereof.

8. The adjustable ostomy wafer system of claim 4, further comprising at least one locking tab that engages the groove of the insert ring, thereby maintaining a position of the insert ring in the adjustable layer.

9. The adjustable ostomy wafer system of claim 4, wherein the insert ring comprises a plurality of grooves, and wherein each of the grooves corresponds to a different level of convexity of the adjustable layer.

10. The adjustable ostomy wafer system of claim 1, wherein the convexity of the adjustable layer is variable between a minimal convexity and a maximal convexity, and wherein the maximal convexity is about one inch.

11. The adjustable ostomy wafer system of claim 1, further comprising an internal adhesive layer that at least partially covers the body-facing surface of the adjustable layer.

12. The adjustable ostomy wafer system of claim 1, wherein the adjustable layer provides a barrier or seal against effluent, thereby ensuring effluent flows only through the effluent opening.

13. A method of using the adjustable ostomy wafer system of claim 1, the method comprising contacting a flush stoma or a retracted stoma with the ostomy wafer.

14. A kit comprising:
   a. an ostomy wafer comprising an adjustable layer, with an effluent opening through which effluent flows, wherein the adjustable layer has a body-facing side and a non-body-facing side; and
   b. a plurality of insert rings capable of providing or increasing convexity of the adjustable layer when the insert ring is pressed against the non-body-facing side of the adjustable layer without rotating the insert ring relative to the ostomy wafer;
   wherein a first insert ring and a second insert ring of the plurality of insert rings differ in an aspect selected from diameter, rigidity, height, and a combination thereof.

15. The kit of claim 14, wherein at least one insert ring comprises a groove that engages a portion of the adjustable layer.

16. The kit of claim 15, wherein the first insert ring and the second insert ring each comprise at least one groove.

17. The kit of claim 16, wherein the first insert ring and the second insert ring comprise a different number of grooves.

18. The kit of claim 14, further comprising an ostomy pouch, wherein the ostomy pouch is capable of coupling to a coupling component of the ostomy wafer.

19. The kit of claim 18, wherein the ostomy pouch and the ostomy wafer are provided as separate components before use.

20. The kit of claim 19, wherein the ostomy pouch and the ostomy wafer are connected before use, but the effluent opening and non-body-facing side of the ostomy wafer is exposed before use.

21. The kit of claim 14, wherein each of the insert rings is configured to provide or increase the convexity of the adjustable layer in response to manual application of an axial pushing force on the insert ring.

22. The kit of claim 15, wherein each groove is annular.

23. The adjustable ostomy wafer system of claim 1, wherein the insert ring is configured to provide or increase the convexity of the adjustable layer in response to manual application of an axial pushing force on the insert ring.

24. The adjustable ostomy wafer system of claim 4, wherein the groove is annular.

25. The kit of claim 14, wherein each of the insert rings is separate from the ostomy wafer.

* * * * *